United States Patent [19]
Xin-Liang et al.

[11] Patent Number: 5,591,619
[45] Date of Patent: Jan. 7, 1997

[54] AUREOBASIDIUM PULLULANS XYLANASE, GENE AND SIGNAL SEQUENCE

[75] Inventors: Li Xin-Liang; Lars G. Ljungdahl, both of Athens, Ga.

[73] Assignee: University of Georgia Research Foundation, Inc., Athens, Ga.

[21] Appl. No.: 315,695

[22] Filed: Sep. 30, 1994

[51] Int. Cl.$^6$ ............................ C12N 1/19; C12N 15/55; C12N 15/62; C12P 21/00
[52] U.S. Cl. .................. 435/201; 435/69.1; 435/254.21; 536/23.2; 536/23.4
[58] Field of Search ............................ 435/254.21, 200; 536/23.2, 23.4, 23.74

[56] References Cited

PUBLICATIONS

Achstetter, T. and Wolf, D.H. (1985), "Hormone processing and membrane-bound proteinases in yeast", Embo. J. 4:173–177.
Biely et al., "Soluble chromatogenic substrates for the assay of endo–1,4–β–xylanases and endo–1,4–β–glucanases", Anal. Biochem. (1985) 144:142–146.
Biely, P., "Microbial xylanolytic system", Trends Biotechnol. (1985) 3:286–290.
Black et al. "Structural basis for the kinetic differences between flavocytochromes $b_2$ from the yeasts *Hansenula anomala* and *Saccharomyces cerevisiae*", Biochem. J. (1989) 263:973–976.
Borneman, W.S. et al., "Feruloyl and p–coumaroyl esterases from the anaerobic fungus *Neocallimastix* MC–2: Properties and functions in plant cell wall degradation", In: *Hemicellulose and Hemicellulases*, (M.P. Coughlan and G. Hazelwood, Eds., Portland Press, Cambridge, U.K. (1993) pp. 85–102.
Castanares, A. et al., "Purification and properties of a feruloyl/p–coumaroy lesterase from the fungus *Penicillium pinophilum*", Enzyme Microb. Technol. (1992) 14:875–884.
Chaudhuri, B. et al. "The pro–region of the yeast prepro–α–factor is essential for membrane translocation of human insulin–like growth factor 1 in vivo", Eur. J. Biochem. (1992) 206:793–800.
Christov, L.P. and Prior, B.A., "Esterases of xylan–degrading microorganisms: Production, properties, and significance", Enzyme Microb. Technol. (1993) 15:460–475.
Collins, S.H., "Production of Secreted Proteins in Yeast", in Protein Production by Biotechnology (Harris, T.J. F. ed.), Elsevier (1990) 61–77.
Das, R.C. and Shultz, J.L., "Secretion of heterologous proteins from *Saccharomyces cerevisiae*", Biotechnol. Progress (1987) 3:43–48.
Dean, J.F.D. and Anderson, J.D., "Ethylene biosynthesis–inducing xylanase. II. Purification and physical characterization of the enzyme produced by *Trichoderma viride*", Plant Physiol. (1991) 95:316–323.
Demolder et al., "Efficient synthesis of secreted murine interleukin–2 by *Saccharomyces cerevisiae*: influence of the 3' untranslated regions and codon usage", Gene (1992) 111:207–213.

Emr et al., "An MFα1–SUC2(α–factor–invertase) gene fusion for study of protein localization and gene expression in yeast", Proc. Natl. Acad. Sci. USA (1983) 80:7080–7084.
Eriksson, K.–E.L., and Kirk, T.K., "Biopulping, biobleaching and treatment of kraft bleaching effluents with white–rot fungi", In:*Comprehensive biotechnology*, C.W. Robinson (Ed.), Pergamon Press, Toronto (1985) 4:271–294.
Eriksson, K–E.L., "Swedish developments in biotechnology related to the pulp and paper industry", (1985) TAPPI (Tech. Assoc. Pulp Pap. Ind.), J. 68:46–55.
Filho et al., "The xylan–degrading enzyme systems of *Penicillium capsulatum* and *Talaromyces emersonii*", Biochem. Soc. Trans. (1991) 19:25S.
Gat et al., "Cloning and DNA Sequence of the gene coding for *Bacillus stearothermophilus* T–6 xylanase", Appl. Environ. Microbiol. (1994) 60:1889–1896.
Ghangas et al., "Cloning of a *Thermonospora fusca* xylanase gene and its expression in *Escherichia coli* and *Streptomyces lividans*", J. Bacteriol. (1989) 171:2963–2969.
Gilbert et al., "Homologous catalytic domains in a rumen fungal xylanase: evidence for gene duplication and prokaryotic origin", Mol. Microbiol. (1992) 6(15):2065–2072.
Gilkes et al., "Domains in microbial β–1,4–glycanases: Sequence conservation, function, and enzyme families", Microbiol. Rev. (1991) 55:303–315.
Grabski, A.C. and Jeffries, T.W., "Production, purification, and characterization of β–(1,4)–endoxylanase of *Streptomyces roseisleroticus*", Appl. & Environ. Microbiol. (1991) 57:987–992.
Hartley, R.D., "Phenolic monomers and dimers of plant cell wall and their effects on fiber utilization", In:*Microbial and plant opportunities to improve lignocellulose utilization by ruminants*, Akin et al. (eds.) Elsevier Sci. Publ., Inc., New York (1990) pp. 183–193.
Henrissat et al., "Cellulase families revealed by hydrophobic cluster analysis", Gene (1989) 81:83–95.
Hitzeman et al., "Expression of a human gene for interferon in yeast", Nature (London) (1981) 293:717–722.
Innis et al., "Expression, glycosylation, and secretion of an *Aspergillus* glucoamylase by *Saccharomyces cerevisiae*", Science (1985) 228:21–26.
Ito et al., "Cloning and sequencing of the xynA gene encoding xylanase A of *Aspergillus kawachii*", Biosci, Boitech. Biochem. (1992) 56:906–912.
Jeffries, T.W., "Emerging technology for fermenting D–xylose", Trends Biotechnol (1985) 3:208–212.
Kluepfel et al., "Purification and characterization of a new xylanase (xylanase B) produced by *Streptomyces lividans* 66", Biochem. J. (1990) 267:45–50.

(List continued on next page.)

Primary Examiner—Robert A. Wax
Assistant Examiner—Eric Grimes
Attorney, Agent, or Firm—Greenlee, Winner and Sullivan

[57] ABSTRACT

A xylanase from *Aureobasidium pullulans* having a high specific activity is provided as well as a signal protein for controlling excretion into cell culture medium of proteins to which it is attached. DNA encoding these proteins is also provided.

16 Claims, 4 Drawing Sheets

OTHER PUBLICATIONS

Kniskern et al., "Constitutive and regulated expression of the hepatitis B virus (HBV) preS2+S protein in recombinant yeast", In:*Expression systems and processes for rDNA products*, Hatch et al., (eds.) 1991 pp. 65–75.

Ko et al. (1992), "Site-directed mutagenesis at aspartate and glutamate residues of xylanase from *Bacillus pumilus*", Biochem. J. 288:117–121.

Koyama et al., (1990) "Purification and some properties of xylan–hydrolysing enzymes from *Robillarda* sp. y–20", Enzyme Microb. Technol. 12:218–224.

Leathers, T.D., "Color variants of *Aureobasidium pullulans* overproduce xylanase with extremely high specific activity", Appl. & Environ. Microbiol. p.86 52:1026–1030.

Leathers et al., "Induction and glucose repression of xylanase from a color variant strain of *Aureobasidium pullulans*", Biotechnol. Lett. (1986) 8:867–872.

Leathers et al., "Overproduction and regulation of xylanase in *Aureobasidium pullulans* and *Cryptococcus albidus*", Biotechnol. & Bioeng. Symp. (1984) 14:225–250.

Leathers, T.D., "Amino acid composition and partial sequence of xylanase from *Aureobasidium*", Biotechnol. Lett. (1988) 10:775–780.

Leathers, T.D., "Purification and properties of xylanase from *Aureobasidium*", J. Ind. Microbiol. (1989) 4:341–348.

Li et al., "Purification and characterization of a new xylanase (APX–II) from the fungus *Aureobasidium pullulans*Y–2311–1", Appl. & Environ. Microbiol. (1993) 59:3212–3218.

Li, X. L. and Ljundahl, L.G., "Cloning, sequencing, and regulation of a xylanase gene from the fungus *Aureobasdium pullulans*Y–2311–1", Appl. & Eviron. Microbiol. (1994) 60:3160–3166.

Lowry et al., "Protein measurement with the Folin phenol reagent", J. Biol. Chem. (1951) 193:265–275.

Luthi et al., "Cloning, sequence analysis, and expression of genes encoding xylan–degrading enzymes from the therophile *Caldocellum saccharolyticum*", Appl. & Environ. Microbiol. (1990) 56:1017–1024.

Marten, M.R. and Seo, J.S. (1991) "Engineering studies of protein secretion in recombinant *Saccharomyces cerevisiae*", In: Expression Systems and Processes for rDNA Products (Hatch et al., eds.), Am. Chem. Soc., Washington, DC.

Miller, G.L., "Use of Dinitrosalicylic acid reagent for determination of reducing sugar", Anal. Chem. (1959) 31:426–428.

Moreau et al., "Secretion of a *Cryptococcus albidus*xylanase in *Saccharomyces cerevisiae*", Gene (1992) 116:109–113.

Myers et al., "Fungal pretreatment of aspen chips improves strength of refiner mechanical pulp", TAPPI (1988) 71:105–108.

Noé et al., "Action of xylanases on chemical pulp fibers. Part II: Enzymatic beating", J. Wood Chem. Technol. (1986) 6:167–184.

Orlean et al., "Analysis of glycoproteins from *Saccharomyces cerevisiae*", Methods in Enzymol. (1991) 194:682–696.

Pacitti et al. "High level expression and purification of the enzymatically active cytoplasmic region of human CD45 phosphatase from yeast", Biochimica et Biophysica Acta (1994) 1222:277–286.

Penttila et al., "Expression of two *Trichoderma reesei*endoglucanases in the yeast *Saccharomyces cerevisiae*", Yeast (1987) 3:175–185.

Rawn, D.J., "RNA Processing", Biochemistry, pp. 781–820, Neil Patterson publishers, Carolina Biological Supply Company, Burlington, NC (1989).

Shareck et al., "Sequences of three genes specifying xylanases in *Streptomyces lividans*", (1991) Gene 107:75–82.

Shepherd et al., "Substrate specificity and mode of action of the cellulases from the theromophilic fungus *Thermoascus aurantiacus*", Biochem J. (1981) 193:67–74.

Sreekrishna, K., "Strategies for optimizing protein expression and secretion in the methylotrophic yeast *Phichia pastoris*", in Baltz et al. (eds.) Industrial Microorganisms: Basic and Applied Molecular Genetics, American Society for Microbilogy, Washington, D.C. (1993) 119–126.

Sterjiades et al., "Extracellular laccases and peroxidases from sycamore maple (*Acer pseudoplatanus*) cell suspension cultures. Reactions with monolignols and lignin model compounds", Planta (1993) 190:75–87.

Teeri et al., "Homologous domains in *Trichoderma reesei*-cellulolytic enzymes: gene sequence and expression of cellobiohydrolase II", Gene (1987) 51:43–52.

Tremblay, L. and Archibald, F., "Production of a cloned xylanase in *Bacillus cereus*and its performance in kraft pulp prebleaching", Can. J. Microbiol. (1993) 39:853–860.

Vainio et al., "Cloning and Expression of *Hormoconis resinae* glucoamylase P cDNA in *Saccharomyces cerevisiae*", Curr. Genet. (1993) 24:38–44.

Van den Hondel et al., "Heterologous gene expression in filamentous fungi", (1991) In: Bennett, J.W. and Lasure, L.L. (eds.), More gene manipulations in fungi, Academic Press, Inc. 396–428.

Wong et al., "Multiplicity of $\beta$–1,4–xylanase in microorganisms. Functions and applications", Microbiol. Rev. (1988) 52:305–317.

Yang et al., "The impact of xylanase on belaching of kraft pulps", Tappi J. (1992) 75:95–101.

Davis, M.A. and Hynes, M.J. (1991) "Regulatory Circuits in *Aspergillus nidulans*", In: J.W. Bennett and L.L. Lasure (eds.) More Gene Manipulations in Fungi., Academic Press, Inc.; pp. 151–189.

Erikksson et al. (1990) "Microbial and enzymatic degradation of wood and wood components", Springer–Verlag, New York, pp. 186–213.

Glick, B.R. and Pasternak, J.J. (1994) "Molecular Biotechnology –Principles and Applications of Recombinant DNA", ASM Press, Washington, D.C., pp. 119–122.

Jurasek, L. and Paice, M.G. (1988) "Biological bleaching of pulp", In; *International pulp bleaching conference*, TAPPI Proceedings Atlanta, GA, pp. 11–13.

Kantelinen et al. (1988) "Hemicellulases and their potential role in bleaching", In: *International pulp bleaching conference*, TAPPI Proceedings Atlanta, GA, pp. 1–9.

Lake, B.D. and Goodwin, H.J. (1976) "Lipids", In I. Smith and J.W.T. Seakins (ed.), Chromatographic and electrophoretic techniques, vol. 1, 4th Ed. Pitman Press, Bath, England, pp. 345–366.

Royer, J.C. and Nakas, J.P. (1990) "Simple, sensitive zymogram technique for detection of xylanase activity in polyacrylamide gels", *Appl. Environ. Microbiol.* 56:1516–1517.

Simpson, H.D. et al. (1991) "An extremely thermostable xylanase from the thermophilic eubacterium *Thermotoga*", *Biochem. J.* 227:413–417.

Tremblay, L. and Archibald, F. (1993) "Production of a cloned xylanase in *Bacillus cereus* and its peformance in Kraft pulp prebleaching", Can. J. Microbiol. 39:853–860.

Ci et al., Abstr. Gen. Meet. Am. Soc. Microbiol. 93:328 (1993).

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
( A ) LENGTH: 68 amino acids
( B ) TYPE: amino acid
( C ) STRANDEDNESS:
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:1:

```
Ala  Gly  Pro  Gly  Gly  Ile  Asn  Tyr  Val  Gln  Asn  Tyr  Asn  Gly  Asn  Leu
1                  5                            10                           15

Gly  Gln  Phe  Thr  Tyr  Asn  Glu  Asn  Ala  Gly  Thr  Tyr  Ser  Met  Tyr  Trp
                   20                          25                      30

Asn  Asn  Gly  Val  Asn  Gly  Asp  Phe  Val  Val  Gly  Leu  Gly  Trp  Ser  Thr
```

```
                    3 5                         4 0                         4 5

Gly  Ala  Ala  Arg  Ser  Ile  Thr  Tyr  Ser  Ser  Asn  Tyr  Gln  Ala  Ser  Gly
             5 0                        5 5                        6 0

Gly  Ser  Tyr  Leu
        6 5
```

( 2 ) INFORMATION FOR SEQ ID NO:2:

( i ) SEQUENCE CHARACTERISTICS:
        ( A ) LENGTH: 45 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:2:

```
        Ala  Gly  Pro  Gly  Gly  Ile  Asp  Tyr  Val  Gln  Asn  Tyr  Asn  Gly  Asn  Leu
        1                   5                        1 0                       1 5

Gly  Gln  Phe  Thr  Tyr  Asn  Glu  Asn  Ala  Gly  Thr  Tyr  Ser  Met  Tyr  Trp
                       2 0                       2 5                       3 0

Asn  Asn  Gly  Val  Asn  Gly  Asp  Phe  Val  Val  Gly  Leu  Gly
                  3 5                       4 0                       4 5
```

( 2 ) INFORMATION FOR SEQ ID NO:3:

( i ) SEQUENCE CHARACTERISTICS:
        ( A ) LENGTH: 70 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:3:

```
        Gly  Thr  Asp  Gly  Gly  Tyr  Tyr  Ser  Phe  Trp  Thr  Asp  Gly  Ala  Gly
        1                   5                        1 0                       1 5

Asp  Ala  Asp  Ala  Thr  Tyr  Gln  Asn  Asn  Gly  Gly  Gly  Ser  Tyr  Thr  Leu
                       2 0                       2 5                       3 0

Thr  Trp  Ser  Gly  Asn  Asn  Lys  Asn  Leu  Val  Gly  Gly  Lys  Gly  Trp  Asn
                  3 5                       4 0                       4 5

Pro  Gly  Ala  Ala  Ser  Arg  Ser  Ile  Ser  Tyr  Ser  Gly  Thr  Tyr  Gln  Pro
             5 0                        5 5                       6 0

Asn  Gly  Asn  Ser  Tyr  Leu
        6 5                  7 0
```

( 2 ) INFORMATION FOR SEQ ID NO:4:

( i ) SEQUENCE CHARACTERISTICS:
        ( A ) LENGTH: 69 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:4:

```
Ala Ser Ala Ala Ser Thr Asp Tyr Trp Gln Asn Trp Thr Asp Gly Gly
 1               5                  10                  15

Gly Ile Val Asn Ala Val Asn Gly Ser Gly Gly Asn Tyr Ser Val Asn
            20                  25                  30

Trp Gly Asn Thr Gly Asn Phe Val Val Gly Lys Gly Trp Thr Thr Gly
        35                  40                  45

Ser Pro Phe Arg Thr Ile Asn Tyr Asn Ala Gly Val Trp Ala Pro Asn
    50                  55                  60

Gly Asn Gly Tyr Leu
65
```

( 2 ) INFORMATION FOR SEQ ID NO:5:

( i ) SEQUENCE CHARACTERISTICS:
        ( A ) LENGTH: 65 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:5:

```
Thr Gly Thr Asp Gly Met Tyr Tyr Ser Phe Trp Thr Asp Gly Gly Gly
 1               5                  10                  15

Ser Val Ser Met Thr Leu Asn Gly Gly Gly Ser Tyr Ser Thr Gln Trp
            20                  25                  30

Arg Asn Cys Gly Asn Phe Val Ala Gly Lys Gly Trp Ser Thr Gly Asp
        35                  40                  45

Gly Asn Val Arg Tyr Asn Gly Tyr Phe Asn Pro Val Gly Asn Gly Tyr
    50                  55                  60

Gly
65
```

( 2 ) INFORMATION FOR SEQ ID NO:6:

( i ) SEQUENCE CHARACTERISTICS:
        ( A ) LENGTH: 66 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:6:

```
Gly Thr Asn Asn Gly Tyr Tyr Tyr Ser Phe Trp Thr Asp Ser Gln Gly
 1               5                  10                  15
```

|     |     |     |     |     |     |     |     |     |     |     |     |     |     |     |
| --- | --- | --- | --- | --- | --- | --- | --- | --- | --- | --- | --- | --- | --- | --- |
| Thr | Val | Ser | Met<br>20 | Asn | Met | Gly | Ser<br>25 | Gly | Gly | Gln | Tyr | Ser | Thr<br>30 | Ser | Trp |
| Arg | Asn | Thr<br>35 | Gly | Asn | Phe | Val | Ala<br>40 | Gly | Lys | Gly | Trp | Ala<br>45 | Asn | Gly | Gly |
| Arg | Arg<br>50 | Thr | Val | Gln | Tyr | Ser<br>55 | Gly | Ser | Phe | Asn | Thr | Ser<br>60 | Gly | Asn | Ala |
| Tyr | Leu<br>65 |

( 2 ) INFORMATION FOR SEQ ID NO:7:

( i ) SEQUENCE CHARACTERISTICS:
        ( A ) LENGTH: 66 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:7:

|     |     |     |     |     |     |     |     |     |     |     |     |     |     |     |     |
| --- | --- | --- | --- | --- | --- | --- | --- | --- | --- | --- | --- | --- | --- | --- | --- |
| Gly<br>1 | Tyr | Ser | Asn | Gly<br>5 | Tyr | Tyr | Ser | Tyr | Trp<br>10 | Asn | Asp | Gly | His | Ala<br>15 | Gly |
| Val | Thr | Tyr | Thr<br>20 | Asn | Gly | Gly | Phe | Ala<br>25 | Asn | Ala | Thr | Leu | Thr<br>30 | Trp | Ser |
| Asn | Ser | Gly<br>35 | Asn | Phe | Val | Gly | Gly<br>40 | Lys | Gly | Trp | Gln | Pro<br>45 | Gly | Thr | Lys |
| Asn | Lys<br>50 | Val | Ile | Asn | Phe | Ser<br>55 | Gly | Ser | Tyr | Asn | Pro | Asn<br>60 | Gly | Asn | Ser |
| Tyr | Leu<br>65 |

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligonucleotide primer
        ( D N A ) for PCR"

( i i i ) HYPOTHETICAL: NO ( x i ) SEQUENCE DESCRIPTION: SEQ ID NO:8:

TAYGTNCARA AYTAYAA                                                              17

( 2 ) INFORMATION FOR SEQ ID NO:9:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="oligonucleotide primer
        ( D N A ) for PCR"

( i i i ) HYPOTHETICAL: NO ( x i ) SEQUENCE DESCRIPTION: SEQ ID NO:9:

CCRTTRTTCC ARTACAT                                                                                      17

( 2 ) INFORMATION FOR SEQ ID NO:10:

( i ) SEQUENCE CHARACTERISTICS:
          ( A ) LENGTH: 17 base pairs
          ( B ) TYPE: nucleic acid
          ( C ) STRANDEDNESS: single
          ( D ) TOPOLOGY: linear ( i i ) MOLECULE TYPE: other nucleic acid
          ( A ) DESCRIPTION: /desc ="oligonucleotide primer
          ( D N A ) for PCR"

( i i i ) HYPOTHETICAL: NO ( x i ) SEQUENCE DESCRIPTION: SEQ ID NO:10:

GTCGCCATTG ACACCGT                                                                                      17

( 2 ) INFORMATION FOR SEQ ID NO:11:

( i ) SEQUENCE CHARACTERISTICS:
          ( A ) LENGTH: 24 base pairs
          ( B ) TYPE: nucleic acid
          ( C ) STRANDEDNESS: single
          ( D ) TOPOLOGY: linear ( i i ) MOLECULE TYPE: other nucleic acid
          ( A ) DESCRIPTION: /desc ="oligonucleotide primer
          ( D N A ) for PCR"

( i i i ) HYPOTHETICAL: NO ( x i ) SEQUENCE DESCRIPTION: SEQ ID NO:11:

GAAGTCGCCA TTGACACCGT TGTT                                                                              24

( 2 ) INFORMATION FOR SEQ ID NO:12:

( i ) SEQUENCE CHARACTERISTICS:
          ( A ) LENGTH: 19 base pairs
          ( B ) TYPE: nucleic acid
          ( C ) STRANDEDNESS: single
          ( D ) TOPOLOGY: linear ( i i ) MOLECULE TYPE: other nucleic acid
          ( A ) DESCRIPTION: /desc ="oligonucleotide primer
          ( D N A ) for PCR"

( i i i ) HYPOTHETICAL: NO ( x i ) SEQUENCE DESCRIPTION: SEQ ID NO:12:

CGGCACGAGC TCGTGCCGG                                                                                    19

( 2 ) INFORMATION FOR SEQ ID NO:13:

( i ) SEQUENCE CHARACTERISTICS:
          ( A ) LENGTH: 19 base pairs
          ( B ) TYPE: nucleic acid
          ( C ) STRANDEDNESS: single
          ( D ) TOPOLOGY: linear ( i i ) MOLECULE TYPE: other nucleic acid
          ( A ) DESCRIPTION: /desc ="oligonucleotide primer
          ( D N A ) for PCR"

( i i i ) HYPOTHETICAL: NO ( x i ) SEQUENCE DESCRIPTION: SEQ ID NO:13:

GTAGCAAGGT GTCTGACAT                                                                                    19

(2) INFORMATION FOR SEQ ID NO:14:

(i) SEQUENCE CHARACTERISTICS:
        (A) LENGTH: 27 amino acids
        (B) TYPE: amino acid
        (C) STRANDEDNESS:
        (D) TOPOLOGY: linear (ii) MOLECULE TYPE: protein (iii) HYPOTHETICAL: NO (v) FRAGMENT TYPE: N-terminal (xi) SEQUENCE DESCRIPTION: SEQ ID NO:14:

```
Tyr Val Gln Asn Tyr Asn Gly Asn Leu Gly Phe Thr Tyr Asn Glu Asn
 1               5                  10                  15

Ala Gly Thr Tyr Ser Met Tyr Trp Asn Asn Gly
        20                  25
```

(2) INFORMATION FOR SEQ ID NO:15:

(i) SEQUENCE CHARACTERISTICS:
        (A) LENGTH: 954 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: exon
        (B) LOCATION: 1..151

(ix) FEATURE:
        (A) NAME/KEY: intron
        (B) LOCATION: 152..210

(ix) FEATURE:
        (A) NAME/KEY: exon
        (B) LOCATION: 211..954

(ix) FEATURE:
        (A) NAME/KEY: CDS
        (B) LOCATION: join(59..151, 211..783)

(ix) FEATURE:
        (A) NAME/KEY: sig_peptide
        (B) LOCATION: join(59..151, 211..219)

(ix) FEATURE:
        (A) NAME/KEY: mat_peptide
        (B) LOCATION: 220..780

(xi) SEQUENCE DESCRIPTION: SEQ ID NO:15:

```
CGGCACGAGC TCGTGCCGGA TCACATCCAT TCAAACAATA CTTCCAACTC TCTTCAAC         58

ATG AAG TTC TTC GCC ACC ATT GCT GCT CTC GTT GTG GGA GCT GTT GCT        106
Met Lys Phe Phe Ala Thr Ile Ala Ala Leu Val Val Gly Ala Val Ala
-34              -30                 -25                 -20

GCC CCA GTC GCA GAG GCT GAG GCT GAG GCC AGC AGC CCC ATG CTG            151
Ala Pro Val Ala Glu Ala Glu Ala Glu Ala Ser Ser Pro Met Leu
            -15             -10                 -5

GTACGATCTC TTCGATGAAC CATTCTATTC GAGACCATCT TGCTGATCAA ACACAATAG       210

ATC GAA CGT GCC GGT CCC GGT GGC ATC AAC TAC GTC CAG AAC TAC AAC        258
Ile Glu Arg Ala Gly Pro Gly Gly Ile Asn Tyr Val Gln Asn Tyr Asn
 -3      1               5                  10
```

| | | | | | | | | | | | | | | | | |
|---|---|---|---|---|---|---|---|---|---|---|---|---|---|---|---|---|
| GGC | AAC | CTG | GGC | CAG | TTC | ACC | TAC | AAT | GAG | AAC | GCT | GGT | ACC | TAC | TCC | 306 |
| Gly | Asn | Leu | Gly | Gln | Phe | Thr | Tyr | Asn | Glu | Asn | Ala | Gly | Thr | Tyr | Ser | |
| | 15 | | | | 20 | | | | | 25 | | | | | | |
| ATG | TAC | TGG | AAC | AAC | GGT | GTC | AAT | GGC | GAC | TTC | GTC | GTT | GGT | CTC | GGT | 354 |
| Met | Tyr | Trp | Asn | Asn | Gly | Val | Asn | Gly | Asp | Phe | Val | Val | Gly | Leu | Gly | |
| 30 | | | | | 35 | | | | | 40 | | | | | 45 | |
| TGG | TCA | ACC | GGT | GCT | GCC | CGC | TCC | ATC | ACC | TAC | TCT | TCC | AAC | TAC | CAG | 402 |
| Trp | Ser | Thr | Gly | Ala | Ala | Arg | Ser | Ile | Thr | Tyr | Ser | Ser | Asn | Tyr | Gln | |
| | | | | 50 | | | | | 55 | | | | | 60 | | |
| GCC | AGC | GGC | GGT | TCT | TAC | CTG | TCC | GTC | TAC | GGC | TGG | ATC | AAC | AGC | CCC | 450 |
| Ala | Ser | Gly | Gly | Ser | Tyr | Leu | Ser | Val | Tyr | Gly | Trp | Ile | Asn | Ser | Pro | |
| | | | 65 | | | | | 70 | | | | | 75 | | | |
| CAG | GCT | GAG | TAC | TAC | ATT | GTC | GAG | TCT | TAC | GGC | TCG | TAC | AAC | CCT | TGC | 498 |
| Gln | Ala | Glu | Tyr | Tyr | Ile | Val | Glu | Ser | Tyr | Gly | Ser | Tyr | Asn | Pro | Cys | |
| | | 80 | | | | | 85 | | | | | 90 | | | | |
| GGC | GCC | GGT | CAG | TCC | GGT | GTC | ACT | CAG | CTC | GGC | ACC | GTC | TGC | AGC | GAT | 546 |
| Gly | Ala | Gly | Gln | Ser | Gly | Val | Thr | Gln | Leu | Gly | Thr | Val | Cys | Ser | Asp | |
| | 95 | | | | 100 | | | | | 105 | | | | | | |
| GGC | GCT | ACC | TAC | ACC | GTC | TAC | ACC | GAC | ACT | CGT | ACC | AAC | CAG | CCC | TCC | 594 |
| Gly | Ala | Thr | Tyr | Thr | Val | Tyr | Thr | Asp | Thr | Arg | Thr | Asn | Gln | Pro | Ser | |
| 110 | | | | 115 | | | | | 120 | | | | | 125 | | |
| ATC | ACT | GGT | ACT | TCT | ACC | TTC | AAG | CAG | TAC | TGG | TCT | GTC | CGC | CAG | ACT | 642 |
| Ile | Thr | Gly | Thr | Ser | Thr | Phe | Lys | Gln | Tyr | Trp | Ser | Val | Arg | Gln | Thr | |
| | | | | 130 | | | | | 135 | | | | | 140 | | |
| AAG | CGT | ACT | TCC | GGC | ACG | GTC | ACC | ACT | GGC | AAC | CAC | TTT | GCT | TAC | TGG | 690 |
| Lys | Arg | Thr | Ser | Gly | Thr | Val | Thr | Thr | Gly | Asn | His | Phe | Ala | Tyr | Trp | |
| | | | 145 | | | | | 150 | | | | | 155 | | | |
| GCC | AAG | TAC | GGC | TTT | GGC | AAC | TCT | TAC | AAC | TTC | CAG | GTC | ATG | CCT | GTC | 738 |
| Ala | Lys | Tyr | Gly | Phe | Gly | Asn | Ser | Tyr | Asn | Phe | Gln | Val | Met | Pro | Val | |
| | | 160 | | | | | 165 | | | | | 170 | | | | |
| GAG | GCT | TTC | TCT | GGC | ACT | GGT | AGC | GCC | AGT | GTC | ACC | GTC | TCT | TAA | | 783 |
| Glu | Ala | Phe | Ser | Gly | Thr | Gly | Ser | Ala | Ser | Val | Thr | Val | Ser | * | | |
| | 175 | | | | 180 | | | | | 185 | | | | | | |

```
ATGTCGGAAC AAGTGGCTGA ATTTGGATGT TGGAAAGGAG GTTGTTTGGG ATGCGGATGA        843

AACGCTGATG AAGATATGAT GTTGATCTGG TTGTGTCCAT TTATGCTAGC TTGTCATTCG        903

TTAGCACAAA GTAAATGTCA GACACCTTGC TACAAAAAAA AAAAAAAAA A                  954
```

( 2 ) INFORMATION FOR SEQ ID NO:16:

( i ) SEQUENCE CHARACTERISTICS:
        ( A ) LENGTH: 221 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

| | | | | | | | | | | | | | | | |
|---|---|---|---|---|---|---|---|---|---|---|---|---|---|---|---|
| Met | Lys | Phe | Phe | Ala | Thr | Ile | Ala | Ala | Leu | Val | Val | Gly | Ala | Val | Ala |
| -34 | | | | -30 | | | | | -25 | | | | | -20 | |
| Ala | Pro | Val | Ala | Glu | Ala | Glu | Ala | Glu | Ala | Ser | Ser | Pro | Met | Leu | Ile |
| | | | -15 | | | | | -10 | | | | | -5 | | |
| Glu | Arg | Ala | Gly | Pro | Gly | Gly | Ile | Asn | Tyr | Val | Gln | Asn | Tyr | Asn | Gly |
| | | 1 | | | 5 | | | | | 10 | | | | | |
| Asn | Leu | Gly | Gln | Phe | Thr | Tyr | Asn | Glu | Asn | Ala | Gly | Thr | Tyr | Ser | Met |
| 15 | | | | | 20 | | | | | 25 | | | | | 30 |
| Tyr | Trp | Asn | Asn | Gly | Val | Asn | Gly | Asp | Phe | Val | Val | Gly | Leu | Gly | Trp |
| | | | | 35 | | | | | 40 | | | | | 45 | |
| Ser | Thr | Gly | Ala | Ala | Arg | Ser | Ile | Thr | Tyr | Ser | Ser | Asn | Tyr | Gln | Ala |
| | | | 50 | | | | | 55 | | | | | 60 | | |

5,591,619

49                                              50
-continued

```
Ser  Gly  Gly  Ser  Tyr  Leu  Ser  Val  Tyr  Gly  Trp  Ile  Asn  Ser  Pro  Gln
          65                      70                     75

Ala  Glu  Tyr  Tyr  Ile  Val  Glu  Ser  Tyr  Gly  Ser  Tyr  Asn  Pro  Cys  Gly
     80                      85                     90

Ala  Gly  Gln  Ser  Gly  Val  Thr  Gln  Leu  Gly  Thr  Val  Cys  Ser  Asp  Gly
95                       100                    105                         110

Ala  Thr  Tyr  Thr  Val  Tyr  Thr  Asp  Thr  Arg  Thr  Asn  Gln  Pro  Ser  Ile
               115                      120                         125

Thr  Gly  Thr  Ser  Thr  Phe  Lys  Gln  Tyr  Trp  Ser  Val  Arg  Gln  Thr  Lys
               130                      135                    140

Arg  Thr  Ser  Gly  Thr  Val  Thr  Thr  Gly  Asn  His  Phe  Ala  Tyr  Trp  Ala
          145                      150                    155

Lys  Tyr  Gly  Phe  Gly  Asn  Ser  Tyr  Asn  Phe  Gln  Val  Met  Pro  Val  Glu
     160                      165                    170

Ala  Phe  Ser  Gly  Thr  Gly  Ser  Ala  Ser  Val  Thr  Val  Ser
175                      180                    185
```

(2) INFORMATION FOR SEQ ID NO:17:

(i) SEQUENCE CHARACTERISTICS:
        (A) LENGTH: 222 amino acids
        (B) TYPE: amino acid
        (C) STRANDEDNESS:
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:17:

```
Met  Asn  Leu  Arg  Lys  Leu  Arg  Leu  Leu  Phe  Val  Met  Cys  Ile  Gly  Leu
1                   5                        10                         15

Thr  Leu  Ile  Leu  Thr  Ala  Val  Pro  Ala  His  Ala  Arg  Thr  Ile  Thr  Asn
               20                      25                         30

Asn  Glu  Met  Gly  Asn  His  Ser  Gly  Tyr  Asp  Tyr  Glu  Leu  Trp  Lys  Asp
          35                      40                         45

Tyr  Gly  Asn  Thr  Ser  Met  Thr  Leu  Asn  Asn  Gly  Gly  Ala  Phe  Ser  Ala
     50                      55                         60

Gly  Trp  Asn  Asn  Ile  Gly  Asn  Ala  Leu  Phe  Arg  Lys  Gly  Lys  Lys  Phe
65                       70                      75                         80

Asp  Ser  Thr  Arg  Thr  His  His  Gln  Leu  Gly  Asn  Ile  Ser  Ile  Asn  Tyr
               85                      90                         95

Asn  Ala  Ser  Phe  Asn  Pro  Ser  Gly  Asn  Ser  Tyr  Leu  Cys  Val  Tyr  Gly
               100                     105                    110

Trp  Thr  Gln  Ser  Pro  Leu  Ala  Glu  Tyr  Tyr  Ile  Val  Asp  Ser  Trp  Gly
          115                     120                    125

Thr  Tyr  Arg  Pro  Thr  Gly  Ala  Tyr  Lys  Gly  Ser  Phe  Tyr  Ala  Asp  Gly
     130                     135                    140

Gly  Thr  Tyr  Asp  Ile  Tyr  Glu  Thr  Thr  Arg  Val  Asn  Gln  Pro  Ser  Ile
145                     150                     155                         160

Ile  Gly  Ile  Ala  Thr  Phe  Lys  Gln  Tyr  Trp  Ser  Val  Arg  Gln  Thr  Lys
               165                     170                         175

Arg  Thr  Ser  Gly  Thr  Val  Ser  Val  Ser  Ala  His  Phe  Arg  Lys  Trp  Glu
               180                     185                    190

Ser  Leu  Gly  Met  Pro  Met  Gly  Lys  Met  Tyr  Glu  Thr  Ala  Phe  Thr  Val
```

|     |     |     |     |     | 195 |     |     |     |     | 200 |     |     |     |     | 205 |     |     |
| --- | --- | --- | --- | --- | --- | --- | --- | --- | --- | --- | --- | --- | --- | --- | --- | --- | --- |
| Glu | Gly | Tyr | Gln | Ser | Ser | Gly | Ser | Ala | Asn | Val | Met | Thr | Asn |
|     |     | 210 |     |     |     |     | 215 |     |     |     |     | 220 |     |

( 2 ) INFORMATION FOR SEQ ID NO:18:

( i ) SEQUENCE CHARACTERISTICS:
        ( A ) LENGTH: 236 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:18:

| Met | Lys | Leu | Ser | Lys | Ile | Lys | Lys | Val | Leu | Ser | Gly | Thr | Val | Ser | Ala |
| --- | --- | --- | --- | --- | --- | --- | --- | --- | --- | --- | --- | --- | --- | --- | --- |
| 1 |     |     |     | 5   |     |     |     |     | 10  |     |     |     |     | 15  |     |
| Leu | Met | Ile | Ala | Ser | Ala | Ala | Pro | Val | Val | Ala | Ser | Ala | Ala | Asp | Gln |
|     |     |     | 20  |     |     |     |     | 25  |     |     |     |     | 30  |     |     |
| Gln | Thr | Arg | Gly | Asn | Val | Gly | Gly | Tyr | Asp | Tyr | Glu | Met | Trp | Asn | Gln |
|     |     | 35  |     |     |     |     | 40  |     |     |     |     | 45  |     |     |     |
| Asn | Gly | Gln | Gly | Gln | Ala | Ser | Met | Asn | Pro | Gly | Ala | Gly | Ser | Phe | Thr |
|     | 50  |     |     |     |     | 55  |     |     |     |     | 60  |     |     |     |     |
| Cys | Ser | Trp | Ser | Asn | Ile | Glu | Asn | Phe | Leu | Ala | Arg | Met | Gly | Lys | Asn |
| 65  |     |     |     |     | 70  |     |     |     |     | 75  |     |     |     |     | 80  |
| Tyr | Asp | Ser | Gln | Lys | Lys | Asn | Tyr | Lys | Ala | Phe | Gly | Asn | Ile | Val | Leu |
|     |     |     |     | 85  |     |     |     |     | 90  |     |     |     |     | 95  |     |
| Thr | Tyr | Asp | Val | Glu | Tyr | Thr | Pro | Arg | Gly | Asn | Ser | Tyr | Met | Cys | Val |
|     |     |     | 100 |     |     |     |     | 105 |     |     |     |     | 110 |     |     |
| Tyr | Gly | Trp | Thr | Arg | Asn | Pro | Leu | Met | Glu | Tyr | Tyr | Ile | Val | Glu | Gly |
|     |     | 115 |     |     |     |     | 120 |     |     |     |     | 125 |     |     |     |
| Trp | Gly | Asp | Trp | Arg | Pro | Pro | Gly | Asn | Asp | Gly | Glu | Val | Lys | Gly | Thr |
|     | 130 |     |     |     |     | 135 |     |     |     |     | 140 |     |     |     |     |
| Val | Ser | Ala | Asn | Gly | Asn | Thr | Tyr | Asp | Ile | Arg | Lys | Thr | Met | Arg | Tyr |
| 145 |     |     |     |     | 150 |     |     |     |     | 155 |     |     |     |     | 160 |
| Asn | Gln | Pro | Ser | Leu | Asp | Gly | Thr | Ala | Thr | Phe | Pro | Gln | Tyr | Trp | Ser |
|     |     |     |     | 165 |     |     |     |     | 170 |     |     |     |     | 175 |     |
| Val | Arg | Gln | Thr | Ser | Gly | Ser | Ala | Asn | Asn | Gln | Thr | Asn | Tyr | Met | Lys |
|     |     |     | 180 |     |     |     |     | 185 |     |     |     |     | 190 |     |     |
| Gly | Thr | Ile | Asp | Val | Thr | Lys | His | Phe | Asp | Ala | Trp | Ser | Ala | Ala | Gly |
|     |     | 195 |     |     |     |     | 200 |     |     |     |     | 205 |     |     |     |
| Leu | Asp | Met | Ser | Gly | Thr | Leu | Tyr | Glu | Val | Ser | Leu | Asn | Ile | Glu | Gly |
|     | 210 |     |     |     |     | 215 |     |     |     |     | 220 |     |     |     |     |
| Tyr | Arg | Ser | Asn | Gly | Ser | Ala | Asn | Val | Lys | Ser | Val |
| 225 |     |     |     |     | 230 |     |     |     |     | 235 |     |

( 2 ) INFORMATION FOR SEQ ID NO:19:

( i ) SEQUENCE CHARACTERISTICS:
        ( A ) LENGTH: 206 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:19:

| Val | Ala | Leu | Ala | Arg | Ser | Pro | Leu | Met | Leu | Pro | Gly | Thr | Ala | Gln | Ala |
|---|---|---|---|---|---|---|---|---|---|---|---|---|---|---|---|
| 1 | | | | 5 | | | | | 10 | | | | | 15 | |
| Asp | Thr | Val | Val | Thr | Thr | Asn | Gln | Glu | Gly | Thr | Asn | Asn | Gly | Tyr | Tyr |
| | | | 20 | | | | | 25 | | | | | 30 | | |
| Tyr | Ser | Phe | Trp | Thr | Asp | Ser | Gln | Gly | Thr | Val | Ser | Met | Asn | Met | Gly |
| | | 35 | | | | | 40 | | | | | 45 | | | |
| Ser | Gly | Gly | Gln | Tyr | Ser | Thr | Ser | Trp | Arg | Asn | Thr | Gly | Asn | Phe | Val |
| | 50 | | | | | 55 | | | | | 60 | | | | |
| Ala | Gly | Lys | Gly | Trp | Ala | Asn | Gly | Gly | Arg | Arg | Thr | Val | Gln | Tyr | Ser |
| 65 | | | | | 70 | | | | | 75 | | | | | 80 |
| Gly | Ser | Phe | Asn | Pro | Ser | Gly | Asn | Ala | Tyr | Leu | Ala | Leu | Tyr | Gly | Trp |
| | | | | 85 | | | | | 90 | | | | | 95 | |
| Thr | Ser | Asn | Pro | Leu | Val | Glu | Tyr | Tyr | Ile | Val | Asp | Asn | Trp | Gly | Thr |
| | | | 100 | | | | | 105 | | | | | 110 | | |
| Tyr | Arg | Pro | Thr | Gly | Glu | Tyr | Lys | Gly | Thr | Val | Thr | Ser | Asp | Gly | Gly |
| | | 115 | | | | | 120 | | | | | 125 | | | |
| Thr | Tyr | Asp | Ile | Tyr | Lys | Thr | Thr | Arg | Val | Asn | Lys | Pro | Ser | Val | Glu |
| | 130 | | | | | 135 | | | | | 140 | | | | |
| Gly | Thr | Arg | Thr | Phe | Asp | Gln | Tyr | Trp | Ser | Val | Arg | Gln | Ser | Lys | Arg |
| 145 | | | | | 150 | | | | | 155 | | | | | 160 |
| Thr | Gly | Gly | Thr | Ile | Thr | Thr | Gly | Asn | His | Phe | Asp | Ala | Trp | Ala | Arg |
| | | | | 165 | | | | | 170 | | | | | 175 | |
| Ala | Gly | Met | Pro | Leu | Gly | Asn | Phe | Ser | Tyr | Tyr | Met | Ile | Met | Ala | Thr |
| | | | 180 | | | | | 185 | | | | | 190 | | |
| Glu | Gly | Tyr | Gln | Ser | Ser | Gly | Thr | Ser | Ser | Ile | Asn | Val | Gly |
| | | 195 | | | | | 200 | | | | | 205 | |

( 2 ) INFORMATION FOR SEQ ID NO:20:

( i ) SEQUENCE CHARACTERISTICS:
( A ) LENGTH: 216 amino acids
( B ) TYPE: amino acid
( C ) STRANDEDNESS:
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:20:

| Arg | Gly | Phe | Leu | Gly | Gly | Ala | Gly | Thr | Leu | Ala | Leu | Ala | Thr | Ala | Ser |
|---|---|---|---|---|---|---|---|---|---|---|---|---|---|---|---|
| 1 | | | | 5 | | | | | 10 | | | | | 15 | |
| Gly | Leu | Leu | Leu | Pro | Gly | Thr | Ala | His | Ala | Ala | Thr | Thr | Ile | Thr | Thr |
| | | | 20 | | | | | 25 | | | | | 30 | | |
| Asn | Gln | Thr | Gly | Thr | Asp | Gly | Met | Tyr | Tyr | Ser | Phe | Trp | Thr | Asp | Gly |
| | | | 35 | | | | | 40 | | | | | 45 | | |
| Gly | Gly | Ser | Val | Ser | Met | Thr | Leu | Asn | Gly | Gly | Gly | Ser | Tyr | Ser | Thr |
| | 50 | | | | | 55 | | | | | 60 | | | | |
| Gln | Trp | Thr | Asn | Cys | Gly | Asn | Phe | Val | Ala | Gly | Lys | Gly | Trp | Ser | Thr |
| 65 | | | | | 70 | | | | | 75 | | | | | 80 |

```
Gly Asp Gly Asn Val Arg Tyr Asn Gly Tyr Phe Asn Pro Val Gly Asn
                85              90                  95

Gly Tyr Gly Cys Leu Tyr Gly Trp Thr Ser Asn Pro Leu Val Glu Tyr
            100             105                 110

Tyr Ile Val Asp Asn Trp Gly Ser Tyr Arg Pro Thr Gly Thr Tyr Lys
        115             120              125

Gly Thr Val Ser Ser Asp Gly Gly Thr Tyr Asp Ile Tyr Gln Thr Thr
    130             135                 140

Arg Tyr Asn Ala Pro Ser Val Glu Gly Thr Lys Thr Phe Gln Gln Tyr
145             150              155                         160

Trp Ser Val Arg Gln Ser Lys Val Thr Ser Gly Ser Gly Thr Ile Thr
            165             170                     175

Thr Gly Asn His Phe Asp Ala Trp Ala Arg Ala Gly Met Asn Met Gly
            180             185             190

Gln Phe Arg Tyr Tyr Met Ile Met Ala Thr Glu Gly Tyr Gln Ser Ser
        195             200             205

Gly Ser Ser Asn Ile Thr Val Ser
    210             215
```

( 2 ) INFORMATION FOR SEQ ID NO:21:

( i ) SEQUENCE CHARACTERISTICS:
      ( A ) LENGTH: 208 amino acids
      ( B ) TYPE: amino acid
      ( C ) STRANDEDNESS:
      ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:21:

```
Lys Asn Phe Leu Val Gly Leu Ser Ala Ala Leu Met Ser Ile Ser Leu
1               5                   10                  15

Phe Ser Ala Thr Ala Ser Ala Ala Ser Thr Asp Tyr Trp Gln Asn Trp
            20              25                  30

Thr Asp Gly Gly Gly Ile Val Asn Ala Val Asn Gly Ser Gly Gly Asn
        35              40                  45

Tyr Ser Val Asn Trp Ser Asn Thr Gly Asn Phe Val Val Gly Lys Gly
    50              55                  60

Trp Thr Thr Gly Ser Pro Phe Arg Thr Ile Asn Tyr Asn Ala Gly Val
65              70              75                      80

Trp Ala Pro Asn Gly Asn Gly Tyr Leu Thr Leu Tyr Gly Trp Thr Arg
                85              90                  95

Ser Pro Leu Ile Glu Tyr Tyr Val Val Asp Ser Trp Gly Thr Tyr Arg
            100             105                 110

Pro Thr Gly Thr Tyr Lys Gly Thr Val Lys Ser Asp Gly Gly Thr Tyr
        115             120             125

Asp Ile Tyr Thr Thr Thr Arg Tyr Asn Ala Pro Ser Ile Asp Gly Asp
    130             135                 140

Arg Thr Thr Phe Thr Gln Tyr Trp Ser Val Arg Gln Ser Lys Arg Pro
145             150             155                         160

Thr Gly Ser Asn Ala Thr Ile Thr Phe Thr Asn His Val Asn Ala Trp
            165             170                 175
```

```
         Lys  Ser  His  Gly  Met  Asn  Leu  Gly  Ser  Asn  Trp  Ala  Tyr  Gln  Val  Met
                        180                      185                      190

Ala  Thr  Glu  Gly  Tyr  Gln  Ser  Ser  Gly  Ser  Ser  Asn  Val  Thr  Val  Trp
                        195                      200                      205
```

( 2 ) INFORMATION FOR SEQ ID NO:22:

( i ) SEQUENCE CHARACTERISTICS:
        ( A ) LENGTH: 236 amino acids
        ( B ) TYPE: amino acid
        ( C ) STRANDEDNESS:
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:22:

```
         Asn  Pro  Ala  Pro  Thr  Ser  Thr  Gly  Thr  Val  Pro  Ser  Ser  Ser  Ala  Gly
         1                   5                        10                      15

Gly  Ser  Thr  Ala  Asn  Gly  Lys  Lys  Phe  Thr  Val  Gly  Asn  Gly  Gln  Asn
                        20                       25                      30

Gln  His  Lys  Gly  Val  Asn  Asp  Gly  Phe  Ser  Tyr  Glu  Ile  Trp  Leu  Asp
                   35                       40                      45

Asn  Thr  Gly  Gly  Asn  Gly  Ser  Met  Thr  Leu  Gly  Ser  Gly  Ala  Thr  Phe
              50                       55                      60

Lys  Ala  Glu  Trp  Asn  Ala  Ala  Val  Asn  Arg  Gly  Asn  Phe  Leu  Ala  Arg
         65                       70                      75                           80

Arg  Gly  Leu  Asp  Phe  Gly  Ser  Gln  Lys  Lys  Ala  Thr  Asp  Tyr  Asp  Tyr
                             85                       90                      95

Ile  Gly  Leu  Asp  Tyr  Ala  Ala  Thr  Tyr  Lys  Gln  Thr  Ala  Ser  Ala  Ser
                        100                      105                     110

Gly  Asn  Ser  Arg  Leu  Cys  Val  Tyr  Gly  Trp  Phe  Gln  Asn  Arg  Gly  Leu
                        115                      120                     125

Asn  Gly  Val  Pro  Leu  Val  Glu  Tyr  Tyr  Ile  Ile  Glu  Asp  Trp  Val  Asp
              130                      135                     140

Trp  Val  Pro  Asp  Ala  Gln  Gly  Lys  Met  Val  Thr  Ile  Asp  Gly  Ala  Gln
         145                      150                      155                          160

Tyr  Lys  Ile  Phe  Gln  Met  Asp  His  Thr  Gly  Pro  Thr  Ile  Asn  Gly  Gly
                             165                      170                     175

Ser  Glu  Thr  Phe  Lys  Gln  Tyr  Phe  Ser  Val  Arg  Gln  Gln  Lys  Arg  Thr
                        180                      185                     190

Ser  Gly  His  Ile  Thr  Val  Ser  Asp  His  Phe  Lys  Glu  Trp  Ala  Lys  Gln
                   195                      200                     205

Gly  Trp  Gly  Ile  Gly  Asn  Leu  Tyr  Glu  Val  Ala  Leu  Asn  Ala  Glu  Gly
              210                      215                     220

Trp  Gln  Ser  Ser  Gly  Val  Ala  Asp  Val  Thr  Leu  Leu
         225                      230                     235
```

( 2 ) INFORMATION FOR SEQ ID NO:23:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: other nucleic acid (A) DESCRIPTION: /desc ="oligonucleotide primer used
    for the amplification of PCR products for xynA expression (iii) HYPOTHETICAL: NO (xi) SEQUENCE DESCRIPTION: SEQ ID NO:23:

CACACAAGCT TATGGCCGGT CCCGGTGGCA TCAA  34

(2) INFORMATION FOR SEQ ID NO:24:

(i) SEQUENCE CHARACTERISTICS:
    (A) LENGTH: 32 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc ="oligonucleotide primer used
        for amplification of PCR products for xynA expression"

(iii) HYPOTHETICAL: NO (xi) SEQUENCE DESCRIPTION: SEQ ID NO:24:

CACAGAAGCT TGATCACATC CATTCAAACA AT  32

(2) INFORMATION FOR SEQ ID NO:25:

(i) SEQUENCE CHARACTERISTICS:
    (A) LENGTH: 32 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc ="oligonucleotide primer used
        for the amplification of PCR products for xynA expression (iii) HYPOTHETICAL: NO (xi) SEQUENCE DESCRIPTION: SEQ ID NO:25:

CCTTCGGATC CTAGCAAGGT GTCTGACATT TA  32

(2) INFORMATION FOR SEQ ID NO:26:

(i) SEQUENCE CHARACTERISTICS:
    (A) LENGTH: 94 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc ="oligonucleotide primer used
        for the amplification of PCR products for xynA expression (iii) HYPOTHETICAL: NO (xi) SEQUENCE DESCRIPTION: SEQ ID NO:26:

ACAGAAGCTT ATATGATGCT TTTGCAAGCC TTCCTTTTCC TTTTGGCTGG TTTTGCAGCC  60

AAAATATCTG CAGCCGGTCC CGGTGGCATC AACT  94

(2) INFORMATION FOR SEQ ID NO:27:

(i) SEQUENCE CHARACTERISTICS:
    (A) LENGTH: 91 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc ="oligonucleotide primer used
        for the amplification of PCR products for xynA expression ( i i i ) HYPOTHETICAL: NO ( x i ) SEQUENCE DESCRIPTION: SEQ ID NO:27:

```
ACAGAAGCTT AAAGAATGAG ATTTCCTTCA ATTTTTACTG CAGTTTTATT CGCATCCTCC    60
GCATTAGCTG CCGGTCCCGG TGGCATCAAC T                                  91
```

AUREOBASIDIUM PULLULANS XYLANASE, GENE AND SIGNAL SEQUENCE

This invention was made, at least in part, with funding from the U.S. Department of Energy (Grant Nos. DE-FG09-86ER13614 and DE-FG05-93ER20127). The United States Government may have certain rights in this invention.

FIELD OF THE INVENTION

This invention pertains to a xylanase of *Aureobasidium pullulans*, the gene encoding this xylanase, and the signal sequence which may be used in recombinant constructs to increase fermentation yield in *Saccharomyces cerevisiae*.

BACKGROUND OF THE INVENTION

Hemicellulose, second only to cellulose in abundance on earth, consists of xylan as the main constituent. Xylan is a hetero-polymer possessing β-1,4 linked xylose units as a backbone with side chains containing pentose and hexose, and acetyl groups. Of these groups some of the arabinoses are esterified by p-coumaric and ferulic acids of lignin (Hartley, R. D., "Phenolic monomers and dimers of plant cell wall and their effects on fiber utilization," In: *Microbial and plant opportunities to improve lignocellulosic utilization by ruminants*, Akin, D. E. et al. (eds.) Elsevier Sci. Publ., Inc., New York (1990) pp. 183–193). Enzymes, particularly xylanase (EC3.2.1.8) which breaks the backbone of xylan, have received great attention for application in industries such as pulp bleaching, Eriksson, K-E. L., "Swedish developments in biotechnology related to the pulp and paper industry," (1985) TAPPI (Tech. Assoc. Pulp Pap. Ind.) 68:46–55; Jurasek, L. and Paice, M. G., "Biological bleaching of pulp", In: *International pulp bleaching conference*, TAPPI, Atlanta, Ga. (1988) pp. 11–13; Kantelinen, A. et al., "Hemicellulases and their potential role in bleaching," In: *International pulp bleaching conference*, TAPPI, Atlanta, Ga. (1988) pp. 1–9; Noé, P. et al., "Action of xylanases on chemical pulp fibers. Part II: Enzymatic beating," J. Wood Sci. Technol. (1986) 6:167–184; and Yang, J. L. et al., "The impact of xylanase on bleaching of kraft pulps," TAPPI J. (1992) 75:95–101), pretreatment of animal feed (Wong, K. et al., "Multiplicity of β-1,4-xylanase in microorganisms. Functions and applications," Microbiol. Rev. (1988) 52:305–317), food processing (Biely, P., "Microbial xylanolytic system," Trends Biotechnol. (1985) 3:286–290), and conversion of lignocellulose into feedstock chemicals and fuels (Jeffries, T. W., "Emerging technology for fermenting D-xylose," Trends Biotechnol. (1985) 3:208–212; Mohandas, D. V. et al., "Development of xylose-fermenting yeasts for ethanol production at high acetic acid concentrations," Sixteenth Symp. on Biotech. for Fuels and Chemicals, Gatlinburg, Tenn. (1994) Paper 16; Lu, Z. and Tsao, G. T., "Fermentation of xylose to glycerol by fungi," Sixteenth Symp. on Biotech. for Fuels and Chemicals, Gatlinburg, Tenn. (1994) Poster 35). One of the challenges for applying xylanase to the above processes is to produce large quantities of highly active enzymes at low cost.

Enzymatic conversion of xylan to its monomeric components requires the participation of several enzymes including xylanase (EC3.2.1.8), β-xylosidase (EC3.2.1.37), α-L-arabinofuranosidase (EC3.2.1.55), α-glucuronidase (EC3.2.1.1), acetyl xylan esterase (EC3.1.1.6) as well as p-coumaroyl and feruloyl esterases (Borneman, W. S. et al., "Feruloyl and p-coumaroyl esterases from the anaerobic fungus Neocallimstix MC-2: Properties and functions in plant cell wall degradation," In: *Hemicellulose and Hemicellulases*, (M. P. Coughlan and G. Hazelwood, Eds., Portland Press, Cambridge, U.K.) (1993) pp. 85–102; Castanares, A. et al., "Purification and properties of a feruloyl and p-coumaroyl esterase from the fungus *Penicillium pinophilum*," Enzyme Microb. Technol. (1992) 14:875–884; Christov, L. P. and Prior, B. A., "Esterases of xylan-degrading microorganisms: Production, properties, and significance," Enzyme Microb. Technol. (1993) 15:460–475; Eriksson, K.-E. L. et al., "Microbial and enzymatic degradation of wood and wood components," Springer-Verlag, New York (1990)).

Xylanases are the key enzymes for the breakdown of xylan since they depolymerize the backbone. They have broad potential applications in wood biopulping (Eriksson, K.-E. L., "Swedish developments in biotechnology related to the pulp and paper industry," TAPPI (1985) 68:46–55; Eriksson, K.-E. L., and Kirk, T. K., "Biopulping, biobleaching and treatment of kraft bleaching effluents with white-rot fungi," In: *Comprehensive biotechnology*, C. W. Robinson (Ed.), Pergamon Press, Toronto (1985) 3:271–294; and Myers, G. C. et al., "Fungal pretreatment of aspen chips improves strength of refiner mechanical pulp," TAPPI (1988) 71:105–108), pulp bleaching (Jurasek, L. and Paice, M. G., "Biological bleaching of pulp", In: *International pulp bleaching conference*, TAPPI, Atlanta, Ga. (1988) pp. 11–13; Kantelinen, A. et al., "Hemicellulases and their potential role in bleaching," In: *International pulp bleaching conference*, TAPPI, Atlanta, Ga. (1988) pp. 1–9; Noé, P. et al., "Action of xylanases on chemical pulp fibers. Part II: Enzymatic beating," J. Wood Sci. Technol. (1986) 6:167–184; Yang, J. L. et al., "The impact of xylanase on bleaching of kraft pulps," TAPPI J. (1992) 75:95–101), pretreatment of animal feed (Wong, K. K. Y. et al., "Multiplicity of β-1,4-xylanase in microorganisms. Functions and applications," Microbiol. Rev. (1988) 52:305–317), food processing (Biely, P., "Microbial xylanolytic system," Trends Biotechnol. (1985) 3:286–290), and for the conversion of lignocellulosic material into industrial feedstock chemicals and fuels (Eriksson, K.-E. L., "Swedish developments in biotechnology related to the pulp and paper industry," TAPPI (1985) 68:46–55; Jeffries, T. W., "Emerging technology for fermenting D-xylose," Trends Biotechnol. (1985) 3:208–212).

Considering the industrial potentials of xylanases, an important aspect of xylanase research is to obtain highly active xylanases at low cost. Consequently several bacteria and fungi have been screened for xylanolytic activity (Eriksson, K.-E. L. et al., "Microbial and enzymatic degradation of wood and wood components," Springer-Verlag, New York (1990); Gilkes, N. R. et al., "Domains in microbial β-1,4-glycanase: Sequence conservation, function, and enzyme families," Microbiol. Rev. (1991) 55:303–315). What has become evident is that these microorganisms produce multiple xylanases with varying specific activities.

The fungus *Aureobasidium pullulans* Y-2311-1 has been shown to produce the highest levels of xylanase among several xylanolytic fungi (Leathers, T. D., "Color variants of *Aureobasidium pullulans* overproduce xylanase with extremely high specific activity," Appl. Environ. Microbiol. (1986) 52:1026–1030; Leathers et al., "Induction and glucose repression of xylanase from a color variant strain of *Aureobasidium pullulans*," Biotechnol. Lett. (1986) 8:867–872; Leathers et al., "Overproduction and regulation of xylanase in *Aureobasidium pullulans* and *Cryptococcus albidus*", Biotechnol. Bioeng. Symp. (1984) 14:225–250). Unfractionated extracellular xylanase from this fungus has been used successfully for the bleaching of kraft pulps (Yang et al., "The impact of xylanase on bleaching of kraft pulps," TAPPI (1992) 75:95–101). D-Xylose, xylobiose, xylan, and arabinose all induced, while glucose repressed, xylanase activity (Leathers, T. D. et al., "Induction and glucose repression of xylanase from a color variant strain of *Aureobasidium pullulans*," Biotechnol. Lett. (1986) 8:867–872). Leathers (Leathers, T. D., "Color variants of *Aureobasidium pullulans* overproduce xylanase with extremely high specific activity," Appl. Environ. Microbiol., (1986) 52:1026–1030) showed that two xylanases with similar molecular masses were secreted into the culture supernatant by *A. pullulans* grown on xylan or xylose, and one of these, which we designated APX-I and which had high specific activity toward oat spelt xylan (OSX), was purified (Leathers, T. D., "Amino acid composition and partial sequence of xylanase from Aureobasidium", Biotechnol. Lett. (1988) 10:775–780; Leathers, T. D., "Purification and properties of xylanase from Aureobasidium," J. Ind. Microbiol. (1989) 4:341–348).

Other organisms which produce xylanases include *Streptomyces lividans* (Kluepfel, D., et al., "Purification and characterization of a new xylanase (xylanase B) produced by *Streptomyces lividans* 66," Biochem. J. (1990) 267:45–50); *Thermoascus aurantiacus* (Shepherd, M. G. et al., "Substrate specificity and mode of action of the cellulases from the thermophilic fungus *Thermoascus aurantiacus*," Biochem J. (1981) 193:67–74); Thermotoga sp. strain Fj SS3-B.1 (Simpson, H. D. et al., "An extremely thermostable xylanase from the thermophilic eubacterium Thermotoga," Biochem. J. (1991) 227:413–417); *Penicillium capsulatum* and *Talaromyces emersonii* (Filho, E. X. et al., "The xylan-degrading enzyme systems of *Penicillium capsulatum* and *Talaromyces emersonii*," Biochem. Soc. Trans. (1991) 19:25S); *Caldocellum saccharolyticum* (Luthi, E. et al., "Cloning, sequence analysis, and expression of genes encoding xylan-degrading enzymes from the thermophile *Caldocellum saccharolyticum*," Appl. Environ. Microbiol. (1990) 56:1017–1024); *Bacillus stearothermophilus* (Gat, O. et al, "Cloning and DNA sequence of the gene coding for *Bacillus stearothermophilus* T-6 xylanase," Appl. Environ. Microbiol. (1994) 60:1889–1896); and *Thermonospora fusca* (Ghangas, G. S. et al., "Cloning of a *Thermonospora fusca* xylanase gene and its expression in *Escherichia coli* and *Streptomyces lividans*," J. Bacteriol. (1989) 171:2963–2969).

Yeast (*Saccharomyces cerevisiae*) has been widely used as a host organism for the production of heterologous proteins such as enzymes, structural proteins, hormones, interferons, and cytokines (Collins, S. H., "Production of Secreted Proteins in Yeast," in Protein Production by Biotechnology (Harris, T. J. R. ed.), Elsevier (1990) 61–77; Hitzeman, R. A. et al., "Expression of a human gene for interferon in yeast," Nature (London) (1981) 293:717–722; Innis, M. A. et al., "Expression, glycosylation, and secretion of an *Aspergillus glucoamylase* by *Saccharomyces cerevisiae*", Science (1985) 228:21–26; Marten and Seo (1991) "Engineering studies of protein secretion in recombinant *Saccharomyces cerevisiae*," In: Expression Systems and Processes for rDNA Products (Hatch, R. T., et al. eds.); Kniskern, P. J. et al., "Constitutive and regulated expression of the hepatitis B virus (HBV) preS2+S protein in recombinant yeast," In: *Expression systems and processes for rDNA products*, R. T. Hatch, C. Goochee, A. Moreira and Y. Alroy (eds.) 1991; and Demolder, J. et al., "Efficient synthesis of secreted murine interleukin -2 by *Saccharomyces cerevisiae*: influence of the 3' untranslated regions and codon usage," Gene (1992) 111:207–213). A xylanase gene from *Cryptococcus albidus* has been expressed in *S. cerevisiae* (Moreau, A. et al., "Secretion of a *Cryptococcus albidus* xylanase in *Saccharomyces cerevisiae*", Gene (1992) 116:109–113). Unlike bacteria, yeast does not produce endotoxins, and products from yeast are considered safe for uses in pharmaceutical and food products. Another advantage of using yeast as a host organism for heterologous protein production is that large-scale production and downstream processing of the organism and its products are readily established considering that this organism is the most commonly used organism for fermentation. Moreover, with the advance of molecular biology, genetic manipulation of yeast has become as routine as genetic manipulation of bacteria. Furthermore, most pharmaceutically and industrially important eukaryotic proteins require post-translational modifications during translocation through the endoplasmic reticulum (ER) and cell membrane. These modifications include proper folding, glycosylation, disulfate bond formation, and proteolysis. Yeast has a secretion system similar to higher eukaryotes. Most importantly, proteins secreted into yeast culture medium are protected from aggregation and protease degradation and more easily purified since yeast itself does not secrete a lot of proteins into culture medium.

Other organisms have been used for expression of foreign xylanase genes. A *B. subtilis* xylanase gene was expressed in *B. cereus* and used for pretreatment of pulp in a papermaking process. (Tremblay, L. and Archibald, F., "Production of a cloned xylanase in *Bacillus cereus* and its performance in Kraft pulp prebleaching," Can. J. Microbiol. (1993) 39:853–860).

Secretion of proteins is facilitated by hydrophobic-residue-rich short signal peptides on the N-terminal regions of protein precursors. Several secreted yeast proteins and peptides including invertase and mating factor α pheromone (α factor) have been shown to possess such signal peptides. These signal peptides are cleaved by specific peptidases during the secretion process. A number of heterologous proteins when fused to these yeast signal peptides are often retained in periplasmic space or secreted into culture medium at low yield (Das, R. C. and Shultz, J. L., "Secretion of heterologous proteins from *Saccharomyces cerevisiae*", Biotechnol. Progress (1987) 3:43–48; Marten and Seo (1991) "Engineering studies of protein secretion in recombinant *Saccharomyces cerevisiae*," In: Expression Systems and Processes for rDNA Products (Hatch, R. T., et al. eds.) Chaudhuri, B. et al., "The pro-region of the yeast prepro-α-factor is essential for membrane translocation of human insulin-like growth factor 1 in vivo," Eur. J. Biochem. (1992) 206:793–800).

Work upon which the present application is based in part has been published in Li, Xin-Liang et al. (1993), "Purificiation and Characterization of a New Xylanase (APX II) from the Fungus *Aureobasidium pullulans* Y-2311-1," Applied and Environmental Microbiology 59:3212–3218 and Li, Xin-Liang and Ljungdahl, Lars G (1994), "Cloning, Sequencing and Regulation of a Xylanase Gene from the Fungus *Aureobasidium pullulans* Y-2311-1," Applied and Environmental Microbiology 60:3160–3166, both of which are fully incorporated herein by reference.

All publications referred to herein are incorporated herein in their entirety.

There is a need in the art for a high-specific-activity xylanase in pure form which degrades hemicellulose, and for DNA encoding this xylanase to enable methods of producing the xylanase in pure form. There is a further need in the art for an efficient signal sequence for use in *Saccharomyces cerevisiae* fermentation to increase yield by increasing secretion of the product.

SUMMARY OF THE INVENTION

Figure 1:
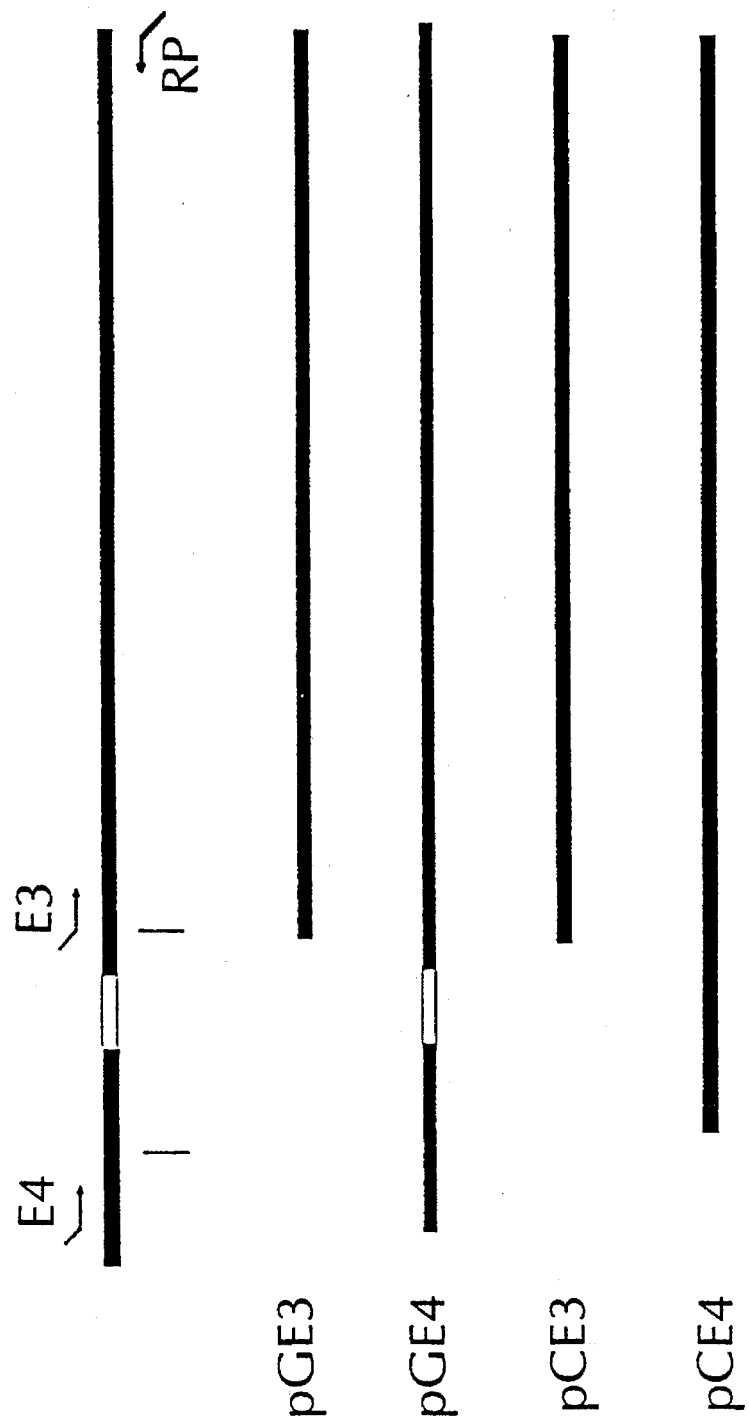
FIG. 1. Primer design and PCR amplification of xynA genomic and cDNA sequences for the expression of xylanase activity in *S. cerevisiae*. Filled and open bars represent xynA exon and intron, respectively. Plasmid names of pYES2 inserted with PCR products are given on the left.

This invention provides a new xylanase (APX-II) possessing high activity towards BWX (birch wood xylan) purified from the culture supernatant of *A. pullulans* Y-2311-1. The $V_{max}$ of this enzyme (2,650 µmol·min$^{-1}$·mg$^{-1}$) as determined from Lineweaver-Burk plots is among the highest reported. The exceptionally high specific activity of this enzyme is an attractive property for biotechnological application of this enzyme. Unfractionated preparations of this enzyme have been successfully used in the biobleaching of pulp at experimental scales by our research group (Yang et al., "The impact of xylanase on bleaching of Kraft pulps," TAPPI (1992) 75:95–101).

The low apparent mass (25 kDa) and the high pI value (9.4) of this enzyme are similar to those of xylanases from *Streptomyces thermoviolaceus* OPC-520 (33 kDa, pI value of 8.0), Robillarda sp. Y-20 (17.6 kDa, pI value of 9.7), *S. lividans* 66 (31 kDa, pI value of 8.4), and *Streptomyces roseiscleroticus* (22.6 kDa, pI value of 9.5). This group of xylanases has been assigned to the category of low-$M_r$, basic xylanases, in contrast to high-$M_r$, acidic xylanases. Most xylanolytic organisms produce both types of xylanases. IEF and zymogram analysis of culture supernatants from *A. pullulans* done in the present study revealed that both acidic (pI value of 4.0) and basic (pI values of 7.3, 7.9, and 9.4) xylanases are produced.

This invention provides a substantially pure mature xylanase protein termed "APX-II" of *A. pullulans*, which has a specific activity of greater than about 2400 toward oat spelt xylan (OSX) under the conditions described in Example 1 and an amino acid sequence as given in Table 5, SEQ ID:15 from amino acid 1 through 187. This xylanase is useful for degrading hemicellulose, for example in pulp bleaching in the paper industry or production of ethanol.

"Substantially pure" as used herein with respect to APX-II means the protein or polypeptide migrates as a single band on SDS-PAGE stained with Coomassie brilliant blue. The protein as purified from *A. pullulans* has a molecular weight of 25 kDa; however the APX-II polypeptide of this invention includes proteins or polypeptides having the same or equivalent amino acid sequence and different amounts of glycosylation.

The term "APX-II" refers to the mature protein or polypeptide having the sequence given in SEQ ID:15 herein, equivalent sequences as defined below, and such sequences preceded with a methionine residue immediately preceding the listed sequence. "Substantially pure" APX-II is substantially free of naturally associated components when separated from the native contaminants which accompany it in its natural state, either when isolated from *A. pullulans* or when recombinantly produced in host cells such as *S. cerevisiae*.

A chemically synthesized APX-II polypeptide protein is considered an "isolated" protein as is the protein isolated from *A. pullulans* or other host cell in which it is recombinantly produced.

"APX-II" as used herein refers to a polypeptide product which exhibits similar biological activities, i.e., has similar specific activity to natural APX-II isolated from *A. pullulans* or chemically synthesized in accordance with the sequence provided in SEQ ID:15 as measured in recognized bioassays, and has substantially the same or "equivalent" amino acid sequence as native APX-II (SEQ ID:15). It will be understood that polypeptides deficient in one or more amino acids in the amino acid sequence reported herein for naturally occurring APX-II, or polypeptides in which one or more amino acids in the amino acid sequence of natural APX-II are replaced by other amino acids are within the scope of the invention and have "equivalent" sequences to that given in SEQ ID:15, provided that they exhibit the functional activity of APX-II, e.g. in terms of having a specific activity of greater than about 2400 toward OSX as measured herein. This invention is intended to embrace all the allelic variations of APX-II. Moreover, as noted above, derivatives obtained by simple modification of the amino acid sequence of the naturally-occurring product, e.g., by way of site-directed mutagenesis or other standard procedures, are included within the scope of the present invention. Forms of APX-II produced by proteolysis of host cells that exhibit similar biological activities to mature, naturally-occurring APX-II are also encompassed by the present invention. The present specification provides guidance to the skilled worker for preparing a large number of equivalent sequences which preferably do not alter areas of homology shared with other xylanases.

The amino acids which occur in the various amino acid sequences referred to in the specification have their usual three- and one-letter abbreviations routinely used in the art, i.e.:

A=Ala=Alanine

C=Cys=Cysteine
D=Asp=Aspartic Acid
E=Glu=Glutamic Acid
F=Phe=Phenylalanine
G=Gly=Glycine
H=His=Histidine
I=Ile=Isoleucine
K=Lys=Lysine
L=Leu=Leucine
M=Met=Methionine
N=Asn=Asparagine
P=Pro=Proline
Q=Gln=Glutamine
R=Arg=Arginine
S=Ser=Serine
T=Thr=Threonine
V=Val=Valine
W=Try=Tryptophan
Y=Tyr=Tyrosine This invention also comprises a signal peptide sequence referred to herein as the APX-II signal peptide. In general, proteins secreted from cells are synthesized as precursor molecules containing hydrophobic N-terminal signal peptides. The signal peptides direct transport of the protein to its target membrane and are then cleaved by a peptidase on the membrane, such as the endoplasmic reticulum, when the protein passes through it.

The APX-II signal peptide of this invention has a sequence as given in Table 5, SEQ ID:15 from amino acid −34 to −1. The term "APX-II signal sequence" encompasses not only the exact sequence given, but also equivalent sequences which have additions, substitutions or deletions which do not interfere with the function of the signal peptide. The coding region for APX-II signal peptide in a construct 5' to the mature APX-II xylanase coding region functions to produce an expression product which more than doubles enzyme activity of the mature APX-II xylanase in S. cerevisiae culture when compared with S. cerevisiae invertase and mating factor alpha pheromone signal sequences placed 5' to the same mature protein and expressed in S. cerevisiae, all as reported herein. The skilled worker, following the teachings hereof, is enabled to make changes to the signal sequence which do not adversely affect its function and thus is enabled to make a large number of operative embodiments of this signal peptide.

This invention also provides for genomic DNA and cDNA encoding the mature APX-II protein or polypeptide and/or signal peptide. The gene encoding both these peptides is termed xynA herein. The DNA sequence of the gene as it occurs in A. pullulans is given in Table 5, SEQ ID:15 from nucleotide 59 to 780. The gene contains an intron shown in Table 5 in small letters, and in SEQ ID:15 from nucleotide 152 to 211 within the coding region for the signal peptide. The DNA sequence including the intron is useful for recombinantly expressing APX-II and signal sequence in Aureobasidium species and other host species capable of splicing out the intron. The xynA gene without the intron is useful for recombinantly expressing APX-II mature protein in S. cerevisiae or other host species which are not capable of splicing out the intron.

Of course, it is recognized by those skilled in the art that the DNA sequences may vary due to the degeneracy of the genetic code and codon usage. All DNA sequences which code for APX-II polypeptide and/or signal peptide are included in this invention, including DNA sequences as given in SEQ ID:15 having an ATG preceding the coding region for the mature protein, and including DNA sequences with and without the intron identified in Table 5.

Additionally, it will be recognized by those skilled in the art that allelic variations may occur in the DNA sequences which will not significantly change activity of the amino acid sequences of the peptides which the DNA sequences encode. All such equivalent DNA sequences are included within the scope of this invention and the definition of the APX-II mature protein coding region and APX-II signal sequence coding region. The skilled artisan will understand that the amino acid sequence of the exemplified APX-II polypeptide and signal peptide can be used to identify and isolate additional, nonexemplified nucleotide sequences which will encode functional equivalents to the polypeptides defined by the amino acid sequences given in SEQ ID:15, or an amino acid sequence of greater than 90% identity thereto and having equivalent biological activity. DNA sequences having at least about 85% homology to the DNA sequences of SEQ ID:15 and encoding polypeptides with the same function are considered equivalent to the sequences of SEQ ID:15 and are included in the definition of "DNA encoding the APX-II mature protein," "the xynA gene" and "the APX-II signal peptide coding region," respectively. Following the teachings herein, the skilled worker will be able to make a large number of operative embodiments having equivalent DNA sequences to those listed herein.

The APX-II signal peptide of this invention may be used to increase yield of foreign genes in host cells in which they are expressed. Any host cell in which the signal sequence is expressed and processed may be used. Preferred host cells are Aurobasidium species and S. cerevisiae, as well as other yeasts known to the art for fermentation, including *Pichia pastoris* (Sreekrishna, K., "Strategies for optimizing protein expression and secretion in the methylotrophic yeast *Pichia pastoris*," in Baltz, R. H., et al. (eds.) Industrial Microorganisms: Basic and Applied Molecular Genetics, AMS Press, Washington, D.C. (1993) 119–126; Glick, B. R. and Pasternak, J. J., "Molecular Biotechnology—Principles and Applications of Recombinant DNA," AMS Press (1994) Washington, D.C.). Filamentous fungi such as Aspergillus, Trichoderma, Penicillium, etc. are also useful host organisms for expression of the DNA of this invention. (Van den Handel, C. et al., "Heterologous gene expression in filamentous fungi," (1991) In: Bennett, J. W. and Lasure, L. L. (eds.), More gene manipulations in fungi, Academy Press, Inc., New York, 397–428). When DNA encoding the APX-II signal peptide is ligated to DNA encoding other proteins expressible in these hosts, the gene products are secreted from these organisms with the help of the signal peptide.

In addition, the coding region for both the signal peptide and the mature APX-II protein may be expressed in such hosts. Alternatively, the APX-II mature protein coding region isolated from the signal sequence may be expressed in such hosts, or the coding region for the signal peptide isolated from the mature protein coding region may be expressed in such hosts.

In a preferred embodiment, vectors suitable for transformation of the host, preferably S. cerevisiae, with the xynA gene, cDNA coding for the APX-II mature protein, or the APX-II signal peptide cDNA coding sequence in combination with a suitable foreign gene expressible in S. cerevisiae, are prepared with the gene under control of a promoter expressible in the host, preferably S. cerevisiae. Preferably sequences from SEQ ID:15 which are 3' to the coding region for the signal peptide are deleted from such constructs. Preferably the promoter is a constitutive promoter such as the yeast enolase promoter (Sangadala et al., (1994) "Preparation and characterization of the site-directed E211Q mutant of yeast enolase," In: Abstracts of University System of Georgia 1994 Research Symposium: Advances in Biotechnology, Georgia State University, Atlanta, Ga., USA) or the yeast alcohol dehydrogenase promoter (Pacitti, A., et al. (1994), "High level expression and purification of the enzymatically active cytoplasmic region of human CD45 phosphatase from yeast," Biochimica et Biophysica Acta 1222:277–286). The vector is used to transform the host either by integration into the chromosome or otherwise. The host organism is then cultured under conditions allowing expression of the gene and the product recovered from the culture medium. Xylanase levels and levels of expression of foreign genes utilizing the signal peptide sequence of this invention are surprisingly high, up to 20 micrograms/ml even without removing the 3' region or using a constitutive promoter.

DETAILED DESCRIPTION OF THE PREFERRED EMBODIMENTS

Aureobasidium pullulans Y-2311-1 produced four major xylanases (EC 3.2.1.8) with pI values of 4.0, 7.3, 7.9, and 9.4 as revealed by isoelectric focusing and zymogram analysis when grown for 4 days on 1.0% oat spelt xylan. The enzyme with a pI of 9.4, called APX-II herein, was purified by ammonium sulfate precipitation, chromatography on a DEAE-Sephadex A-50 column, and gel filtration with a Sephadex G-75 column. The enzyme had a mass of about 25 kDa as determined by both sodium dodecyl sulfate-polyacrylamide gel electrophoresis and gel filtration chromatography. The purified enzyme had a $K_m$ of 7.6 mg·ml$^{-1}$ and a $V_{max}$ of 2,650 µmol·min$^{-1}$·mg$^{-1}$ for birchwood xylan at 28° C. and pH 4.5. It lacked activity towards carboxymethylcellulose, cellobiose, starch, mannan, p-nitrophenyl (pNP)-β-D-xylopyranoside, pNP-β-D-glucopyranoside, pNP-α-D-glucopyranoside, pNP-β-D-cellobioside, pNP-β-D-fucopyranoside, and pNP-α-D-galactopyranoside. The predominant end products of birchwood xylan or xylohexaose hydrolysis were xylobiose and xylose. The enzyme had the highest activity at pH 4.8 and 54° C. Sixty percent of the activity remained after the enzyme had been incubated at 55° C. and pH 4.5 for 30 min. The sequence of the first 68 amino acid residues at the amino terminus showed homology to those of several other xylanases.

APX-II is specific for hydrolyzing natural xylan and is free of cellulase activity, which are desirable properties for biobleaching of pulps. Some xylanases have both xylanase and cellulase activities (Shareck, F. C. R. et al., "Sequences of three genes specifying xylanases in Streptomyces lividans," Gene (1991) 107:75–82). Xylobiose and xylose are produced as end products, while higher oligoxylosaccharides appear to be produced only as intermediates of xylan hydrolysis by this enzyme. No free arabinose is produced from xylan by this enzyme. On the basis of these results, it is safe to say that APX-II is a typical endo-β-1,4-xylanase. In spite of the extremely high specific activity of this enzyme towards xylan, the $K_m$ of this enzyme is similar to that of xylanases from other sources (Grabski, A. C. and Jeffries, T. W., "Production, purification, and characterization of β-(1,4)-endoxylanase of Streptomyces roseiscleroticus," Appl. Environ. Microbiol. (1991) 57:987–992; Kluepfel, D. et al., "Purification and characterization of a new xylanase (xylanase B) produced by Streptomyces lividans 66," Biochem. J. (1990) 267:45–50; Koyama, H. et al., "Purification and some properties of xylan-hydrolysing enzymes from Robillarda sp. Y-20," Enzyme Microb. Technol. 12:218–224). The pH and temperature for optimal enzyme activity of this enzyme are also in the range of those reported for xylanases from other mesophilic fungi and bacteria (Wong, K. et al., "Multiplicity of β-1,4-xylanase in microorganisms. Functions and applications", Microbiol. Rev. (1988) 52:305–317).

Immunoblot analysis with antiserum against APX-II revealed that two protein bands of 25 and 22 kDa are synthesized in xylan- and xylose-grown but not in glucose- or glycerol-grown culture supernatants. The intensity of these two bands was closely correlated with the xylanase activity levels in the supernatants, but the other cross-reactive band (above 100 kDa) was not correlated with the activity levels. The results suggested that the synthesis of APX-II in A. pullulans might be regulated at the transcriptional level rather than at the translational or posttranslational level. Xylose, xylobiose, or their derivatives may be transported into the cell to trigger the transcription process.

The N-terminus of APX-II is homologous to those of xylanases from several other fungi and bacteria. The APX-II N-terminal sequence showed the highest homology to that of a xylanase from S. commune but much lower homology to those of the xylanases from T. harzanium or Cryptococcus albidus. The homology of this sequence to those of xylanases from several bacteria, including B. subtilis and S. lividans, was intermediate. Tyr, Gly, Trp, Asn, Gly, Trp, Gly, and Tyr at positions 8, 17, 32, 34, 43, 46, 65, and 67 of APX-II, respectively, were aligned and conserved in all xylanases. Residues from positions 40 to 51 are highly conserved, indicating the importance of this region for the function of the enzyme.

Although the relationship between APX-I and APX-II is unclear, APX-I (Leathers, T. D., "Amino acid composition and partial sequence of xylanase from Aureobasidium," Biotechnol. Lett. (1988) 10:775–780; Leathers, T. D., "Purification and properties of xylanase from Aureobasidium," J. Ind. Microbiol. (1989) 4:341–348) and APX-II appear to be closely related isozymes. Purified APX-I was reported to have an $M_r$ of 20,000 and a pI value of 8.5 (Leathers, T. D., "Purification and properties of xylanase from Aureobasidium," J. Ind. Microbiol. (1989) 4:341–348), suggesting that APX-I might be the 22-kDa cross-reactive band on our immunoblots and the band with a pI value of 7.9 on our IEF gels.

An 83 bp DNA region of APX-II was amplified using polymerase chain reaction (PCR) and used as a probe for the xylanase cloning. The longest cDNA (xynA) obtained by cDNA cloning and PCR amplification consisted of 895 bp. A. pullulans xynA had an open reading frame (ORF) encoding a polypeptide of 221 amino acids with a calculated mass of 23,531 Da and containing a 34 amino acid signal peptide in front of the amino terminus of the mature enzyme. Strong homology was found between the deduced amino acid sequence of the gene product and some xylanases from bacterial and fungal sources. A. pullulans xynA expression product thus should belong to the family G glycanases. Northern blot analysis revealed that only one transcript of 900 bases was present in cultures grown in medium containing D-xylose or oats spelt xylan (OSX). Transcription was completely repressed in the presence of glucose in the medium. Southern blot analysis indicated that A. pullulans xynA was present as a single copy in the genome. Comparison between the genomic and cDNA sequences revealed that one intron of 59 bp was present in the coding region.

The xynA gene was expressed in *Saccharomyces cerevisiae* and its product secreted into the culture medium. Polymerase chain reaction was used to amplify certain regions of both genomic and cDNA sequences for the expression and secretion studies. *S. cerevisiae* clone pCE4 with the whole open reading frame of xynA inserted in plasmid pYES2 after 4 hr of galactose induction had xylanase activity levels of 6.7 and 26.2 U.ml$^{-1}$ in the cell associated fraction and culture medium, respectively. pCE3 and pGE3 with inserts of cDNA and genomic DNA containing the mature enzyme region preceded by a Met codon only had xylanase activity in the cell associated fraction (1.6 U.ml$^{-1}$). The 34 amino acid signal peptide of xynA supported the post-translational processing of xynA product and the secretion of the active xylanase from *S. cerevisiae*. Neither intracellular nor extracellular xylanase activity was detected in the culture of pGE4 with an insert containing genomic DNA possessing the 59 bp intron of xynA in the signal peptide region, which indicated that the intron was not spliced out properly by *S. cerevisiae*. The first 17 amino acid sequence of the heterologous xylanase isolated from pCE4 culture medium was identical to that of APX-II isolated from *A. pullulans*. It is clear that the signal peptide of xynA was recognized by yeast secretory pathways and was cleaved during secretion. Clones pIN1 and pAF1 with signal peptides of *S. cerevisiae* invertase and mating factor α pheromone fused to the N-terminus of the mature xylanase had 12.6 and 9.7 U.ml$^{-1}$, respectively, whereas pCE4 and pCE3 had 28.6 and 0.34 U.ml$^{-1}$, respectively of xylanase activity in the culture medium after 6 hr of induction. The xylanase-specific mRNA levels among pCE3, pCE4, pIN1 and pAF1 clones were similar. *A. pullulans* xynA signal peptide can be fused to other proteins for secreting high levels of recombinant proteins into culture medium from *S. cerevisiae*.

EXAMPLES

Example 1

Purification and Characterization of APX-II

Chemicals: Reagents for the cultivation of *A. pullulans* Y-311-1 were purchased from Difco Lab. (Detroit, Mich.). Resins for liquid chromatography and gel filtration calibration markers were purchased from Pharmacia LKB Biotechnology (Piscataway, N.J.). Reagents and standard markers for gel electrophoresis and immunoblot analysis were purchased from Bio-Rad Lab. (Richmond, Calif.). Immobilon-P membranes for immunoblot analysis were obtained from Millipore Co. (Bedford, Mass.). All other chemicals were products of Sigma Chemical Co. (St. Louis, Mo.).

Strain and cultivation conditions: *A. pullulans* Y-2311-1 was grown in YM medium (Leathers, T. D., "Color variants of *Aureobasidium pullulans* overproduce xylanase with extremely high specific activity," Appl. Environ. Microbiol. (1986) 52:1026–1030) at 28° C. with shaking (200 rpm). The medium contained 1.0% (w/v) OSX, D-xylose, glucose or glycerol as carbon source. Culture volumes were either 50 or 500 ml. For time course studies, small portions of cultures were sampled using aseptic technique and frozen at −20° C. until analyzed. No loss of xylanase activity at −20° C. was observed over a period of one year.

Enzyme and protein assays: Birch wood xylan (BWX, 1.0%, w/v) was prepared by solubilizing 1 g of BWX in 20 ml 0.2M NaOH. This solution was then adjusted to pH 4.5 by the addition of acetic acid and the volume was adjusted to 100 ml with H$_2$O. Xylanase assay was performed by incubating 500 µl BWX with 50 µl enzyme solution at 28° C. for 15 min. Other substrates (1% or 5 mM) were tested under the same conditions. Reactions were terminated by the addition of either the 3,5-dinitrosalicyclic acid (DNS) reagent for natural substrates, or 1M Na$_2$CO$_3$ for synthetic substrates. Reducing sugars were measured with the DNS reagent (Miller, G. L., "Use of dinitrosalicylic acid reagent for determination of reducing sugar," Anal. Chem. (1959) 31:426–428) using D-xylose as standard. p-Nitrophenol released from synthetic substrates was measured by the absorption increase at 400 nm. One unit of enzyme activity was defined as the amount of enzyme that released 1 µmol of xylose equivalent or p-nitrophenol per min. Protein was measured by using the procedure of Lowry et al., "Protein measurement with the Folin phenol reagent," J. Biol. Chem. (1951) 193:265–275 or the bicinchoninic acid (BCA) micro protein assay kit from Pierce (Rockford, Ill.).

Enzyme purification: Purification of the xylanase was monitored by both the enrichment of a pI 9.4 protein band on isoelectric focusing gels and a 25 kDa protein band detected on sodium dodecyl sulfate-polyacrylamide gel and by an increase in xylanase specific activity. One liter of a 4 day-old culture grown on 1% (w/v) OSX as carbon source was the starting material. *A. pullulans* cells and residual OSX were removed by centrifugation at 5,000× g for 5 min and the supernatant was treated with ammonium sulfate. Proteins which precipitated in the range between 30–50% saturation comprised about 20% of the total xylanase activity. The precipitate was collected by centrifugation at 10,000× g for 20 min and dialyzed against 50 mM sodium phosphate buffer, pH 6.8. The sample was further concentrated by tangential-flow ultrafiltration (Amicom, Inc., Beverly, Mass.) against a membrane (YM3) having an apparent molecular weight cutoff of 3,000. The concentrated enzyme sample (12 ml) was loaded onto a DEAE-Sephadex A-50 column (3.5×20 cm) which had been equilibrated with 50 mM sodium phosphate buffer, pH 6.8. Proteins were eluted with 500 ml each of 50 mM sodium phosphate, pH 6.8, containing 0, 0.5 and 1.0M NaCl. Fractions (2.5 ml) were collected at a flow rate of 0.5 ml.min$^{-1}$, and those with high xylanase activity were pooled. Desalting and equilibration of the pooled enzyme against 50 mM acetate buffer, pH 4.5, was again achieved by using tangential-flow ultrafiltration. The enzyme preparation was loaded onto a G-75 gel filtration column (2×85 cm) and fractions of 2.5 ml were collected at a flow rate of 0.5 ml.min$^{-1}$. Bovine serum albumin (67 kDa), ovalbumin (43 kDa), chymotrypsinogen A (25 kDa) and ribonuclease A (13,7 kDa) (Pharmacia, Piscataway, N.J.) were used as standards to calibrate the column.

Antiserum production: Purified xylanase (100 µg in 100 µl 50 mM sodium acetate buffer, pH 4.5) was emulsified with an equal volume of Hunter's TiterMax™ adjuvant (CytRx, Atlanta, Ga.) and injected into a 4 month-old rabbit. Blood (2 ml) was collected before the injection and once every week after the injection. Antibody titer was determined using ELISA. When the antibody titer reached adequate level (six weeks after the injection) 20 ml blood was drawn every week for 4 more weeks.

Sodium dodecyl sulfate (SDS)-polyacrylamide gel electrophoresis (PAGE), immunoblot analysis and isoelectric focusing (IEF): SDS-PAGE were performed as described by Laemmli (1970). Acrylamide concentration in gels was 12.5% (w/v). Protein bands in the gels were either visualized with Coomassie brilliant blue (CBB) R-250 staining or subjected to immunoblot analysis. Transfer of proteins from gels to Immobilon-P membranes was done for 1 hr at 4° C. in 20 mM Tris/HCl, pH 8.3, 20% (v/v) methanol and 0.1 (w/v) SDS using a Mini Trans-Blot cell (Bio-Rad, Richmond, Calif.). Detection of protein bands with anti-xylanase antiserum was performed using a horseradish peroxidase immunoblot kit (Bio-Rad) according to manufacturer's instructions. Isoelectric focusing was performed as described by Sterjiades et al., "Extracellular laccases and peroxidases from sycamore maple (*Acer pseudoplatanus*) cell suspension cultures. Reactions with monolignols and lignin model compounds," Planta (1993) 190:75–87, on precast gels, pH 3–10 (Precote, Serva Biochemicals, N.J.). Serva protein test mixture 9 was used as standards for determining pI values. The pI markers included amyloglucosidase (3.5), feritin (4.4), bovine albumin (4.7), β-lactoglobulin (5.34), conalbumin (5.9), horse myoglobin (7.3), whale myoglobin (8.3), ribonuclease (9.45), and cytochrome c (10.65). After focusing, proteins were detected by CBB R-250 staining or xylanase activity was detected by zymogram analysis (Royer, J. C. and Nakas, J. P., "Simple, sensitive zymogram technique for detection of xylanase activity in polyacrylamide gels", Appl. Environ. Microbiol. (1990) 56:1516–1517). For zymogram analysis, a gel (0.75 mm thick) containing 0.2% remazol brilliant blue R-D-xylan (RBB-xylan), 1% agarose and 100 mM sodium acetate, pH 4.5, was overlaid on the focusing gel plate. After incubation of the gels at 28° C. for 15 min, the overlay gel was removed and immersed into a solution of 50% (v/v) ethanol and 50 mM sodium acetate, pH 5.0, for incubation overnight at 4° C. Xylanase activity was visualized as clear bands against blue background. Each lane of the original IEF gel was also sliced into 0.25 cm pieces. Each piece was soaked overnight in 0.5 ml 100 mM sodium acetate, pH 4.5, and eluted xylanase activity was assayed under standard conditions.

The crude supernatant samples of *A. pullulans* culture were subjected to IEF. More than ten protein bands were seen after Coomassie blue staining. Four of these bands with pI values at 4.0, 7.3, 7.9 and 9.4 exhibited xylanase activity. Elution of the xylanase active bands from the IEF gel showed these bands contained over 80% of the total activity applied to the gel, distributed as 12% (pI 4.0), 6% (pI 7.3), 36% (pI 7.9) and 30% (pI 9.4).

The xylanase with pI 9.4 was purified to apparent homogeneity. This enzyme, designated APX-II, had a mass of 25,000 Da on SDS-PAGE. Gels (12% [wt/vol]) were loaded with approximately 7 μg of protein after DEAE-Sephadex chromatography or 5 μg of protein after gel filtration. Molecular mass markers included myosin (200 kDa), β-galactosidase (116.25 kDa), phosphorylase (97.4 kDa), bovine serum albumin (66.2 kDa), ovalbumin (45 kDa), carbonic anhydrase (31 kDa), trypsin inhibitor (21.5 kDa), and lysozyme (14.4 kDa). The specific activity (2520 U.mg$^{-1}$) of the purified protein (Table 1) was slightly higher than that (2100 U.mg$^{-1}$) reported for xylanase APX-I (Leathers, T. D. et al., "Overproduction and regulation of xylanase in *Aureobasidium pullulans* and *Cryptococcus albidus*," Biotechnol. Bioeng. Symp. (1984) 14:225–240).

TABLE 1

Purification of xylanase from *A. pullulans*[a]

| Purification step | Total protein (mg) | Total activity (U) | Specific activity (U/mg) | Purification (fold) |
|---|---|---|---|---|
| Culture filtrate | 349.3 | 146,000 | 417 | 1 |
| (NH$_4$)$_2$SO$_4$ precipitation | 18.5 | 28,000 | 1,520 | 3.6 |
| DEAE-Sephadex A-50 | 15.7 | 26,200 | 1,670 | 4.0 |
| Sephadex G-75 | 6.2 | 15,100 | 2,440 | 5.8 |

[a]This purification was from 1 liter of culture grown for 4 days with 1% OSX as the substrate.

After the ammonium sulfate precipitation with 30–50% saturation the 25 kDa band was substantially enriched while the other xylanases stayed in the supernatant. Specific activity of enzyme preparation increased 3.6-fold during this step. Chromatography on DEAE-Sephadex resulted in one peak of xylanase activity which eluted in the flow-through volume. Chromatography on Sephadex G-75, the final step used for the xylanase purification, again resulted in only one peak of xylanase activity. A polypeptide band of about 27 kDa on SDS-PAGE was completely removed during the gel filtration step even though the specific activity of the enzyme preparation did not increase dramatically. The xylanase peak eluted with an apparent mass of 22–25 kDa. The enzyme pooled from peak fractions after gel filtration migrated as a single 25 kDa band on SDS-PAGE stained with CBB.

The purified xylanase was tested for the effect of temperature and pH on the activity. The activity of the purified enzyme was measured under the conditions described above, except that the pH of the reaction mixture was adjusted with either 0.1M sodium acetate buffer (pH 3.1 to 5.4) or 0.1M sodium phosphate buffer (pH 5.8 to 8.2). The initial activity of this enzyme towards BWX was the highest at pH 4.8, and at least 80% the maximal rate was attained from pH 3.8 to 5.4. The purified xylanase gave the highest initial activity at temperature 54° C. towards BWX in 50 mM sodium acetate, pH 4.5. Under these conditions, 50% of the highest activity was obtained at 25° C. and 62° C. The enzyme was fairly stable at temperature up to 50° C. in 50 mM sodium acetate, pH 4.5. After the enzyme was preincubated at 50° C. in 50 mM sodium acetate, pH 4.5, for 4 hours, 73% of the activity was retained. Sixty percent of the activity remained after the enzyme was preincubated at 55° C. for 30 min. This enzyme, however, was not stable at 60° C. Rapid inactivation of enzyme activity was observed at this temperature.

The purified enzyme was assayed for the hydrolytic activity against a variety of natural and synthetic substrates. BWX and OSX were hydrolyzed at similar rates at 28° C. and pH 4.5. Under these conditions, no detectable activity was observed towards carboxymethylcellulose, cellobiose, starch, mannan, p-nitrophenyl (pNP) β-D-xylopyranoside, pNP β-D-glucopyranoside, pNP α-D-glucopyranoside, pNP β-D-cellobioside, pNP β-D-fucopyranoside or pNP α-D-galactopyranoside. A Lineweaver-Burk plot of the activity over a broad concentration range of BWX (0.2–12.0 mg.ml$^{-1}$) showed that the $K_m$ and $V_{max}$ of this enzyme were 7.2 mg xylan.ml$^{-1}$ and 2,650 μmol.min$^{-1}$.mg$^{-1}$ of protein, respectively at 28° C. and pH 4.5.

Hydrolysis products released by the purified xylanase from xylohexaose and OSX were separated by TLC. Enzyme (200 U) was incubated in 50 mM sodium acetate, pH 4.5, at 28° C. with 1% (wt/vol) solubilized OSX for 0, 10 and 30 min and 1.5 and 24 h or with 10 mM xylohexaose at 0, 10 and 30 min and 1.5 and 6 h. Oligoxylosaccharide standards were run under the same conditions. X1, xylose; X2, xylobiose; X3, xylotriose. The predominant end products from OSX hydrolysis were xylobiose and xylose, even though xylotriose was initially produced. This suggested that xylotriose was produced as an intermediate that was eventually cleaved to xylobiose and xylose. It appeared that xylopentaose was also produced from OSX and this product did not disappear with increasing time. No arabinose was detected among the hydrolysis products of OSX. Xylobiose and xylotriose were rapidly generated from xylohexaose and xylotriose was again further hydrolyzed to xylobiose and xylose.

Antiserum was raised against the purified xylanase and immunoblot analysis of xylanase production by cultures grown for 3 days on various substrates was performed. A band with an apparent $M_r$ of 25,000 was found in lanes loaded with purified enzyme, OSX and D-xylose grown cultures, but not in samples from glucose or glycerol grown cultures. Cultures were incubated at 28° C. for 72 h with shaking (150 rpm). Cells and residual insoluble substrates were removed by centrifugation at 8,000× g for 5 min, and supernatants were concentrated 10-fold by ultrafiltration (Centricon-3; Amicon). Aliquots (10 µl) of concentrated supernatants from cultures grown on OSX, xylose, glycerol, or glucose, as well as *T. viride* xylanase (40 U; Sigma) and the purified *A. pullulans* xylanase (2 µg) were analyzed by immunoblotting with the antiserum against purified *A. pullulans* xylanase APX-II. Migrations of prestained SDS-PAGE protein standards (Bio-Rad), including myosin (205 kDa), β-galactosidase (116.5 kDa), phosphorylase B (106 kDa), bovine serum albumin (80 kDa), ovalbumin (49.5 kDa), carbonic anhydrase (32.5 kDa), soybean trypsin inhibitor (27.5 kDa), and lysozyme (18.5 kDa) were used. A high mass (above 100 kDa) band which was cross-reactive with the antiserum was present in all supernatants regardless of the carbon source. A 22 kDa cross reactive band was detected in OSX and xylose grown cultures, but not in those grown in glucose or glycerol. Supernatant xylanase preparation from a *Trichoderma viride* (Dean, J. F. D. and Anderson, J. D., "Ethylene biosynthesis-inducing xylanase. II. Purification and physical characterization of the enzyme produced by *Trichoderma viride*," Plant Physiol. (1991) 95:316–323) culture gave a very faint cross-reactive band at about 20 kDa. Xylanase activity was high in OSX (285 U.ml$^{-1}$) and xylose (91 U.ml$^{-1}$) grown cultures, but was not detectable in glycerol or glucose grown cultures. Xylanase activity levels and the presence of the 25 and 22 kDa bands on immunoblot membranes were highly correlated. Concentrated OSX culture supernatants were compared over 120 hours of incubation time by immunoblot analysis. Supernatant samples, removed at 0 to 120 h of incubation and prepared as described above were subjected to immunoblot analysis with the antiserum against purified *A. pullulans* xylanase APX-II. Samples taken after 0, 12, 36, 48, 72, 96 and 120 h of incubation were analyzed. The 25 kDa xylanase was detected as early as 12 hours after inoculation, and subsequently increased continuously up to 96 hours. The 22 kDa protein appeared in the supernatant 24 hours after inoculation and increased steadily over the remaining 120 hours. The high molecular mass (about 120 kDa) cross-reactive protein first appeared at 24 hours and did not change substantially afterwards. Other minor cross-reactive bands (82 and 30 kDa) were also noted in the supernatant at the late stages of incubation. The xylanase activity levels in the supernatant increased continuously up to 385 U.ml$^{-1}$ after 96 hr of incubation, which matched very well the increase in intensity of the 25 and 22 kDa bands on immunoblot. Reducing sugars in OSX culture increased to 3.4 mg.ml$^{-1}$ in the early period (24 hr) of incubation and decreased rapidly to low level (about 0.5 mg.ml$^{-1}$). Protein concentration maintained relatively stable over the period of incubation, though small changes were recorded.

Example 2

Amino acid analysis and Amino Acid Sequencing of APX-II

Amino acid analysis and amino terminal sequencing: Amino acid analysis of the purified xylanase (0.4 µg) of Example 1 was performed on a 120A amino acid analyzer (Applied Biosystems Inc., Foster City, Calif.). The amino N-terminal amino acid sequencing (3 µg) was performed on an Applied Biosystems 477A gas-phase sequencer equipped with an automatic on-line phenylthiohydantoin derivative analyzer. Homologous peptide sequences were searched and aligned with the N-terminal residues of the purified xylanase by using the GCG programs of the University of Wisconsin on the University of Georgia Bioscience Computing Facility.

Thin layer chromatography (TLC): TLC on silica gel plates (Analtech, Inc., Newark, Del.) was used to analyze the hydrolysis products of xylanase. Alkaline solubilized BWX (1%, w/v) or xylohexaose (10 mM) in 50 mM sodium acetate (pH 4.5) was incubated with 200 U of purified xylanase or crude supernatant enzyme samples at 28° C. Hydrolysis was stopped by heating the reaction solution at 80° C. for 10 min. Aliquots (10 µl) were spotted onto a TLC plate and then partitioned for 2.5 hr at room temperature using chloroform:glacial acetic acid:H$_2$O (6:7:1, v/v). Sugars were visualized by diphenylamine staining as described by Lake and Goodwin (Lake, B. D. and Goodwin, H. J., "Lipids," In I. Smith and J. W. T. Seakins (ed.), Chromatographic and electrophoretic techniques, Vol. 1, 4th ed., Pitman Press, Bath, England (1976) pp. 345–366).

The amino acid composition and the N-terminal amino acid sequence of the purified xylanase are shown in Tables 2 and 3, respectively.

TABLE 2

Amino acid composition of xylanases

| | mol % amino acid for xylanase[a] | | |
| | A. pullulans | | |
| Amino acid | APX-II | APX-I | T. viride |
| --- | --- | --- | --- |
| Ala | 7.78 | 11.38 | 3.9 |
| Arg | 3.09 | 6.61 | 3.7 |
| Asx | 12.64 | 12.81 | 14.3 |
| Cys | 0 | 0 | 0 |
| Glx | 8.29 | 14.58 | 5.0 |
| Gly | 15.90 | 3.93 | 14.6 |
| His | 3.04 | 0 | 1.8 |
| Ile | 2.35 | 4.59 | 4.2 |
| Leu | 2.73 | 0.62 | 3.8 |
| Lys | 2.17 | 16.34 | 1.6 |
| Met | 0.34 | 0 | 0 |
| Phe | 3.11 | 5.54 | 4.3 |
| Pro | 2.40 | 1.96 | 3.3 |
| Ser | 10.78 | 13.24 | 11.8 |
| Thr | 12.07 | 5.73 | 7.7 |
| Trp | ND[b] | ND | 3.9 |
| Tyr | 7.19 | 0.85 | 8.7 |
| Val | 6.42 | 0 | 7.2 |

[a]Data for APX-I and the *T. viride* xylanase are from Leathers, T. D., "Amino acid composition and partial sequence of xylanase from Aureobasidium," Biotechnol. Lett. (1988) 10:775–780 and Dean, J. F. D. and Anderson, J. D., "Ethylene biosynthesis-inducing xylanase. II. Purification and physical characterization of the enzyme produced by *Trichoderma viride*," Plant Physiol. (1991) 95:316–323, respectively.
[b]ND, not determined.

APX-II contained high levels of Gly (15.9%), Asx (12.64%), Thr (12.07%) and Ser (10.78%), but very little Met (0.34%). The amino acid composition of ApxII was similar to that of a *T. viride* xylanase (Dean, J. F. D. and Anderson, J. D. (1991), "Ethylene biosynthesis-inducing xylanase. II Purification and physical characterization of the enzyme produced by *Trichoderma viride*," Plant Physiol. 95:316–323), but substantially different from that of APX-I (Leathers, T. D. et al. (1986), "Induction and glucose repression of xylanase from a color variant strain of *Auerobasidium pullulans*," Biotechnol. Lett. 8:867–872) (Table 2). The first 45 residues at the N-terminus of APX-I and II were the same except that APX-II had Asn instead of Asp at position 7

(Table 3). Homologous sequences to the first sixty eight amino acid residues at the amino terminus of APX-II were searched and retrieved from Swissprot data bank. The sequences included corresponding regions of xylanases from *Schizophyllum commune* (45.6%), *Bacillus subtilis* (38.7%), *Streptomyces lividans* C (36.8%) and B (35.3%), and *Trichoderma harzanium* (32.4%) (Table 3.)

Isolation of DNA and RNA from *A. pullulans*. For isolation of genomic DNA, the fungus was grown in medium containing glucose (1.0%, w/v) for 3 days. Cells were collected by centrifugation (3,000× g, 15 min), and washed twice with $H_2O$ at 4° C. Protoplast formation, disruption of cells and recovery of chromosomal DNA were done according to Black et al. ("Structural basis for the inetic differences

TABLE 3

Alignment of N-terminal amino acid sequence of APX-II with homologous xylanase sequences of
*A. pullulans* (APX-I), *S. commune* (Sc), *B. subtilis* (Bs), *S. lividans* C (SlC) and B (SlB), and
*T. harzanium* (Th). Aligned residues which match those found in APX-II are shown in boldface type.

```
                         10                  20                  30
APX-II (SEQ ID:1)    A G P G G I  N Y V Q N Y N G N L G Q F . . T Y N E N . A G T Y S M Y W. N

APX-I (SEQ ID:2)     A G P G G I  D Y V Q N Y N G N L G Q F . . T Y N E N . A G T Y S M Y W. N

Sc (SEQ ID:3) . . .              G T D G G Y Y Y S F W T D G A . G D A D A T Y Q N N G G G S Y T L T WS G

Bs (SEQ ID:4) . . .              A S A A S T D Y W Q N W T D G G G I V N A . V N G . S G G N Y S V N W. G

SlC (SEQ ID:5) . . .             T G T D G M Y Y S F W T D G G . G S V S M T L N . . G G G S Y S T Q W. R

SlB (SEQ ID:6) . . .             G T N N G Y Y Y S F W T D S Q . G T V S M . . N M G S G G Q Y S T S W. R

Th (SEQ ID:7) . . .              G Y S N G . Y Y S Y W N D G H A G V . . . T Y T N G G F A N A T L T W. S 40                  50                  60
APX-II (SEQ ID:1)    N G V N G D F V V G L G WS T G A A . . R S I T Y S . S N Y Q A S G G S Y L . . .

APX-I (SEQ ID:2)     N G V N G D F V V G L G . . . . . . . . . . . . . . . . . . . . . . . . . . . .

Sc (SEQ ID:3)        N N K N L . . V G G K G W N P G A A S . R S I S Y S G T . Y Q P N G N S Y L . . .

Bs (SEQ ID:4)        N . . T G N F V V G K G W T T G S P . F R T I N Y N A G V W A P N G N G Y L . . .

SlC (SEQ ID:5)       N C . . G N F V A G K G W S T G D G N V R . . . Y N G Y . F N P V G N G Y G . . .

SlB (SEQ ID:6)       N . . T G N F V A G K G W A N G G R . . R T V Q Y S G S . F N T S G N A Y L . . .

Th (SEQ ID:7)        N . . S G N F V G G K G W Q P G T . K N K V I N F S G S . Y N P N G N S Y L . . .
```

Example 3

Cloning of xynA

Strains, vectors, and cultivation conditions. *Aureobasidium pullulans* Y-2311-1 is a color variant strain (Leathers, T. D. et al., "Overproduction and regulation of xylanase in *Aureobasidium pullulans* and *Cryptococcus albidus*," Biotechnol. Bioeng. Symp. (1984) 14:225–250). It was grown at 28° C. with shaking (200 rpm) in YM medium (Leathers, T. D. et al., "Overproduction and regulation of xylanase in *Aureobasidium pullulans* and *Cryptococcus albidus*," Biotechnol. Bioeng. Symp. (1984) 14:225–250) containing 1.0% (w/v) oat spelt xylan (OSX), D-xylose, glucose, or glycerol as carbon source. Under these conditions, the fungus grew morphologically similar to yeast, showing typical cell budding growth pattern. *E. coli* strains used in this study include INVαF', SURE and XL-Blue and vectors, pCRII, λXZAPII, and pBluescript. They were purchased from either Stratagene Cloning Systems, La Jolla or Invitrogene Co., San Diego, Calif.

between flavocytochromes b2 from the yeasts *Hansenula anomula* and *Saccharomyces cerevisiae*," Biochem. J. (1989) 263:973–976). For isolation of RNA as template for cDNA library construction, cells were grown for 3 days on 1.0% (w/v) OSX as carbon source and collected as described above. Diethyl pyrocarbonate (DEPC)-treated sterile $H_2O$ was used to wash the cells. Disruption of cells and extraction of RNA were performed using an RNA isolation kit (Stratagene) following the manufacturer's instructions, with the exception that the cells were broken by shaking (100 rpm) in a water bath at 60° C. with glass beads (212–300μ in size, Sigma Chemical Co., St. Louis, Mo.). Poly(A) RNA was prepared from total RNA by chromatography on oligo (dT) cellulose (Boehringer Mannheim Co., Indianapolis, Ind.). For isolation of RNA used in Northern blot analysis, cells were first grown on 1.0% (v/v) glycerol for 3 days, collected by centrifugation, and washed with DEPC-treated sterile $H_2O$ once. The cells were then suspended in media containing 10 g/l of glucose, or D-xylose, or a mixture 10 g/l each of glucose and D-xylose, or glucose and OSX, and cultured while shaking at 28° C. for 20 hr before RNA isolation.

Primer designs and PCR: Two regions of the APX-II N-terminal amino acid sequence (residue 8–13 and 30–35 SEQ ID:1) were used to design two degenerate nucleotide primers P0813 and P3035 (Table 4) with redundancy of 128 and 8 fold, respectively. Biotin molecules were attached to the 5' ends of these primers during the synthesis by using biotin-ON phosphoramidite (Clontech Lab., Inc., Palo Alto, Calif.). Using genomic DNA as template and the Geneamp PCR reagent kit (Perkin Elmer Co., Norwalk, Conn.), DNA fragments were amplified by PCR. Amplification was performed for 30 cycles on a 480 Thermal Cycler (Perkin Elmer Co.) with each cycle including 30 second melting at 95° C., 30 second annealing at 50° C., and 45 second extension at 72° C. The PCR was also used to amplify the 5' end of the full length xylanase cDNA missing in the positive cDNA clones. Lambda DNA was purified from the liquid cDNA library using a λ DNA purification system (Promega Co., Madison, Wis.) and used as template for the amplification. The T3 promoter sequence and P3338 (Table 4), which was 152 bp from the 5' end of the positive cDNA clones, were used as primers. Amplification was done by 30 cycles with 60 second melting at 95° C., 60 second annealing at 55° C., and 90 second extension at 72° C. PCR products were separated by electrophoresis on agarose gels (2.5 or 4.0%, w/v), and visualized by ethidium bromide staining. PCR products were cloned into the pCRII vector (Invitrogen Co.).

Construction and screening of an *A. pullulans* cDNA library: Oligo (dT) cellulose-purified RNA isolated from cells grown on OSX was used as template for the synthesis of complementary DNA (cDNA). cDNA longer than 400 bp as fractionated by a spin column was ligated into λZAPII arms using a ZAP-cDNA synthesis kit and packaged with the Gigapack II packaging extract according to the manufacturer's instructions (Stratagene Cloning Systems). Recombinant phages were screened for hybridization with the 83 bp biotinylated PCR fragments. Briefly, plaques (1 mm in diameter) grown on top agar were transferred to Photogene nylon membranes (Gibco BRL Life Technologies., Inc., Gaithersburg, Md.) by overlaying the membranes on the top agar for 2 min. Detection of positive clones on the membranes was done using a PhotoGene nucleic acid detection system according to the manufacturer's instruction (Gibco BRL), except that the membranes were incubated in TBS (100 mM Tris/HCl, pH 7.5, 150 mM NaCl) containing 200 μg/ml proteinase K at 37° C. for 1 hr before prehybridization, and 44° C. instead of 50° C. was used for washes with 0.1× sterile sodium citrate (SSC) buffer and 1% (w/v) SDS to achieve hybridization stringency. Positive clones were purified with a second round of screening, and were then converted into the pBluescript SK (–) form by in vivo excision as described by Stratagene.

TABLE 4

| Oligonucleotide primers used in PCR[a] | | |
|---|---|---|
| PO813 | TAT(C)GTT(ACG)CAA(G)AAT(C)TAT(C)AA | (SEQ ID:8) |
| P3035 | CCA(G)TTA(G)TTCCAA(G)TACAT | (SEQ ID:9) |
| P200 | GTCGCCATTGACACCGT | (SEQ ID:10) |
| P3339 | GAAGTCGCCATTGACACCGTTGTT | (SEQ ID:11) |
| PFW | CGGCACGAGCTCGTGCCGG | (SEQ ID:12) |
| PRW | GTAGCAAGGTGTCTGACAT | (SEQ ID:13) |

[a]All primers are from 5' to 3'.

Amplification and cloning of a biotinylated xylanase specific DNA probe: An 83 bp DNA fragment was amplified by the PCR using P0813 and P3035 as primers and *A. pullulans* genomic DNA as template. Reaction solutions (100 μl) with (0.5 ng) and without *A. pullulans* genomic DNA were loaded on a 4.0% (w/v) agarose gel. DNA molecular standards (Gibco BRL) were loaded on a separate lane. After electrophoresis, DNA bands were visualized by ethidium bromide staining. No non-specific band was observed. The PCR product was directly cloned into pCRII. Eight out of ten white colonies had the 83 bp DNA insert as revealed by restriction enzyme digestion and nucleotide sequence analysis. The deduced amino acid sequence, YVQNYNGNLGFTYNENAGTYSMYWNNG (SEQ ID:14), matched the corresponding region of the N-terminal amino acid sequence of Example 2 (Table 3). P0813 and P3035 were re-synthesized with biotin conjugated to their 5' ends. PCR products using these primers were used as hybridization probes for cDNA library screening, Southern, and Northern blot analysis.

Example 4

Sequencing of xynA

Southern and Northern blot analysis. Genomic DNA was digested to completion with various restriction endonucleases purchased from Boehringer Mannheim Co. or New England Biolabs, Inc. (Beverly, Mass.). Digested DNA fragments were separated on a 1.0% (w/v) agarose gel in 1× Tris-acetate/EDTA (TAE) buffer. Biotinylated HindIII digested λ DNA fragments (Gibco BRL) were used as size markers. Total RNA samples and molecular weight standards (Gibco BRL) were separated in 2.0% (w/v) agarose gels in the presence of formaldehyde as described by Sambrook, J. et al. ("Molecular Cloning. A Laboratory Manual," (1989) 2nd ed., Cold Spring Harbor, New York: Cold Spring Harbor Laboratory Press), DNA and RNA fragments in gels were transferred to Photogene nylon membranes by using the vacuum blotter (Bio-Rad Lab., Richmond, Calif.), and cross-linked to the surface of the membrane by UV light in an UV 1800 Stratalinker (Stratagene). The biotinylated PCR fragments were denatured by boiling for 5 min and used as hybridization probes as described for the screening of the cDNA library.

Analysis of genomic DNA. Oligonucleotide primers PFW and PRW (Table 4) corresponding to the 5' and 3' ends of the full length cDNA insert for the *A. pullulans* xylanase were synthesized. Using these oligonucleotides as primers, with genomic DNA and DNA purified from cDNA library as templates, the PCR reactions were performed as described above with the exception that each cycle had a denaturation time of 45 second (95° C.), an annealing time of 45 seconds (55° C.), and an extension time of 1.5 minutes (72° C.). After 30 cycles, reaction solutions (20 μl) were separated on a 2.5% (w/v) agarose gel and DNA bands were visualized by ethidium bromide staining. The PCR products amplified from genomic DNA were cloned into pCRII and sequenced as described above.

A cDNA library was constructed in λZAPII using poly(A) RNA isolated from 3 day old OSX-grown culture. Plaques (approximately 5×10[5]) were screened using the biotinylated PCR fragments. During the first round of screening, five plaques contained DNA that hybridized to these probes. A second round of screening yielded pure clones. All five positive plaques were recovered as pBluescript SK(–) through in vivo excision. All five positive clones had identical restriction patterns. Therefore, only two of these five clones were sequenced. Sequences of both strands of the insert were determined using both universal and specific primers. The PCR fragment was located 106 bp from the beginning of the insert. The insert had 820 bp possessing an 18 base poly (A) tail at the 3' end. Neither xylanase activity nor immunologically cross-reactive polypeptide to the antiserum against APX-II was found in the supernatant or in the sonicated cell fractions of cultures after induction by isopropythio-β-D-galactoside, suggesting that the cDNA was fused out of frame with the lacZ gene.

Based on the N-terminal amino acid sequences of APX-II, Genetic Computing Group (GCG) analysis revealed that this insert encoded a polypeptide of 213 amino acid residues. The Nterminal amino acid Ala of both APX-I and II was located 79 bp from the 5' end of the insert. The deduced amino acid sequence matched the N-terminal amino acid sequences of APX-I and II, with the exception of the Asp at position 7 of APX-I (Leathers, T. D., "Amino acid composition and partial sequence of xylanase from Aureobasidium," Biotechnol. Lett. (1988) 10:775–780). Upstream of the mature N-terminal sequence was an amino acid sequence rich in hydrophobic residues which would serve as a signal peptide for the secretion of the xylanases. No Met residue was, however, found at the amino side of the signal peptide, suggesting these cDNA clones might not represent the full-length cDNA of the gene. Using cDNA library as template, and T3 promoter sequence and P3339 (Table 4) as primers, the missing 5' end of the full length cDNA was amplified by PCR, cloned into pCRII, and sequenced. The full length cDNA designated as xynA contained 895 bp. The nucleotide sequence of xynA is given in Table 5, SEQ ID:15. Table 5 shows nucleotide and deduced amino acid sequences of the complementary and genomic DNA of *A. pullulans* xynA. The N-terminal amino acid sequence of the mature enzyme obtained by protein sequencing is underlined. An intron sequence is shown in lowercase letters. A 34-amino-acid sequence upstream of Ala of the mature enzyme is a putative signal peptide.

TABLE 5 xynA Sequence (SEQ ID:15)

```
  1   CGGCACGAGCTCGTGCCGGATCACATCCATTCAAACAATACTTCCAACTCTCTTCAAC

59   ATGAAGTTCTTCGCCACCATTGCTGCTCTCGTTGTGGGAGCTGTTGCTGCCCCAGTCGCA
       M  K  F  F  A  T  I  A  A  L  V  V  G  A  V  A  A  P  V  A
      -34

119   GAGGCTGAGGCTGAGGCCAGCAGCCCCATGCTGgtacgatctcttcgatgaaccattcta
       E  A  E  A  E  A  S  S  P  M  L 179   ttcgagaccatcttgctgatcaaacacaatagATCGAACGTGCCGGTCCCGGTGGCATCA
                                      I  E  R  A  G  P  G  G  I  N
                                            -1  1

239   ACTACGTCCAGAACTACAACGGCAACCTGGGCCAGTTCACCTACAATGAGAACGCTGGTA
       Y  V  Q  N  Y  N  G  N  L  G  Q  F  T  Y  N  E  N  A  G  T
             10                              20

299   CCTACTCCATGTACTGGAACAACGGTGTCAATGGCGACTTCGTCGTTGGTCTCGGTTGGT
       Y  S  M  Y  W  N  N  G  V  N  G  D  F  V  V  G  L  G  W  S
             30                              40

359   CAACCGGTGCTGCCCGCTCCATCACCTACTCTTCCAACTACCAGGCCAGCGGCGGTTCTT
       T  G  A  A  R  S  I  T  Y  S  S  N  Y  Q  A  S  G  G  S  Y
             50                              60

419   ACCTGTCCGTCTACGGCTGGATCAACAGCCCCCAGGCTGAGTACTACATTGTCGAGTCTT
       L  S  V  Y  G  W  I  N  S  P  Q  A  E  Y  Y  I  V  E  S  Y
             70                              80

479   ACGGCTCGTACAACCCTTGCGGCGCCGGTCAGTCCGGTGTCACTCAGCTCGGCACCGTCT
       G  S  Y  N  P  C  G  A  G  Q  S  G  V  T  Q  L  G  T  V  C
             90                             100

539   GCAGCGATGGCGCTACCTACACCGTCTACACCGACACTCGTACCAACCAGCCCTCCATCA
       S  D  G  A  T  Y  T  V  Y  T  D  T  R  T  N  Q  P  S  I  T
            110                             120

599   CTGGTACTTCTACCTTCAAGCAGTACTGGTCTGTCCGCCAGACTAAGCGTACTTCCGGCA
       G  T  S  T  F  K  Q  Y  W  S  V  R  Q  T  K  R  T  S  G  T
            130                             140

659   CGGTCACCACTGGCAACCACTTTGCTTACTGGGCCAAGTACGGCTTTGGCAACTCTTACA
       V  T  T  G  N  H  F  A  Y  W  A  K  Y  G  F  G  N  S  Y  N
            150                             160

719   ACTTCCAGGTCATGCCTGTCGAGGCTTTCTCTGGCACTGGTAGCGCCAGTGTCACCGTCT
       F  Q  V  M  P  V  E  A  F  S  G  T  G  S  A  S  V  T  V  S
            170                             180                 187

779   CTTAAATGTCGGAACAAGTGGCTGAATTTGGATGTTGGAAAGGAGGTTGTTTGGGATGCG
        *

839   GATGAAACGCTGATGAAGATATGATGTTGATCTGGTTGTGTCCATTTATGCTAGCTTGTC

899   ATTCGTTAGCACAAAGTAAATGTCAGACACCTTGCTACAAAAAAAAAAAAAAAAAA
```

N-terminal amino acid sequence of the mature enzyme obtained by protein sequencing is underlined. An intron sequence is expressed as lower case letters. A 34 amino acid sequence upstream of Ala of the mature enzyme is the signal peptide. The G+C ratio of xynA was 52.5%, which is close to the value of 54% for an *Aspergillus kawachii* xylanase gene (Ito, K. et al., "Cloning and sequencing of the xynA gene encoding xylanase A of *Aspergillus kawachii*," Biosci. Biotech. Biochem. (1992) 56:906–912).

A start codon 59 bp downstream of the 5' end of xynA was identified, which began an open reading frame (ORF) of 666 bp. The codon usage in this ORF was significantly biased to C at the third position (Table 6). The percentage of A, T, G, and C at this position was 20.4, 24.8, 24.4, and 29.7%, respectively. These ratios are typical properties of highly expressed genes in fungi (Ito, K. et al., "Cloning and sequencing of the xynA gene encoding xylanase A of *Aspergillus kawachii*," Biosci. Biotech. Biochem. (1992) 56:906–912; Moreau, A. et al., "Secretion of a *Cryptococcus albidus* xylanase in *Saccharomyces cerevisiae*," Gene (1992) 116:109–113; Teeri, T. T. et al., "Homologous domains in *Trichoderma reesei* cellulolytic enzymes: gene sequence and expression of cellobiohydrolase II," Gene (1987) 51:43–52).

TABLE 6

Codon usage of *A. pullulans* xynA

| Amino acid | Codon | Usage | Amino acid | Codon | Usage |
| --- | --- | --- | --- | --- | --- |
| Gly | GGG | 0 | Thr | ACG | 1 |
|  | GGA | 1 |  | ACA | 0 |
|  | GGT | 12 |  | ACT | 8 |
|  | GGC | 15 |  | ACC | 13 |
| Glu | GAG | 7 | Trp | TGG | 5 |
|  | GAA | 1 | Met | ATG | 4 |
| Gln | CAG | 10 | Cys | TGT | 0 |
|  | CAA | 0 |  | TGC | 2 |
| Asp | GAT | 1 | Tyr | TAT | 0 |
|  | GAC | 2 |  | TAC | 19 |
| Asn | AAT | 2 | Leu | TTG | 0 |
|  | AAC | 14 |  | TTA | 0 |
| Val | GTG | 1 |  | CTG | 3 |
|  | GTA | 0 |  | CTA | 0 |
|  | GTT | 3 |  | CTT | 0 |
|  | GTC | 15 |  | CTC | 3 |
| Ala | GCG | 0 | Phe | TTT | 2 |
|  | GCA | 1 |  | TTC | 7 |
|  | GCT | 12 | Ser | AGT | 1 |
|  | GCC | 9 |  | AGC | 6 |
| Lys | AAG | 4 |  | TCG | 1 |
|  | AAA | 0 |  | TCA | 1 |
| Ile | ATA | 0 |  | TCT | 8 |
|  | ATT | 2 |  | TCC | 7 |
|  | ATC | 5 | His | CAT | 0 |
| Arg | AGG | 0 |  | CAC | 1 |
|  | AGA | 0 | Pro | CCG | 0 |
|  | CGG | 0 |  | CCA | 1 |
|  | CGA | 0 |  | CCT | 2 |
|  | CGT | 3 |  | CCC | 4 |
|  | CGC | 2 |  |  |  |

The ORF encoded a polypeptide of 221 amino acid residues with a calculated mass of 23,531 Da. The putative signal peptide contained 34 amino acid residues, rich in hydrophobic residues. The mature polypeptide consisted of 187 amino acid residues with a calculated mass of 20,016 Da, which is very close to the value of 20 kDa determined for APX-I (Leathers, T. D., "Purification and properties of xylanase from Aureobasidium," J. Industr. Microbiol. (1989) 4:341–348), but smaller than the 25 kDa determined for APX-II. The deduced amino acid composition of this ORF together with that determined for APX-II is shown in Table 7.

TABLE 7

Amino acid composition of *A. pullulans* xylanase[a]

| Amino acid | Whole ORF | Mature enzyme | APX-II[b] |
| --- | --- | --- | --- |
| Ala | 22 | 12 | 14 |
| Arg | 5 | 4 | 5 |
| Asx | 19 | 19 | 23 |
| Cys | 2 | 2 | 0 |
| Glx | 18 | 14 | 15 |
| Gly | 28 | 27 | 29 |
| His | 1 | 1 | 5 |
| Ile | 7 | 5 | 4 |
| Leu | 6 | 5 | 5 |
| Lys | 4 | 3 | 4 |
| Met | 4 | 2 | 1 |
| Phe | 9 | 7 | 6 |
| Pro | 7 | 5 | 5 |
| Ser | 24 | 22 | 20 |
| Thr | 22 | 21 | 22 |
| Trp | 5 | 5 | ND[c] |
| Tyr | 19 | 19 | 13 |
| Val | 19 | 15 | 11 |
| Total | 221 | 187 | 182 |

[a]Number of molecules/mole of enzyme.
[b]Calculated from the mole percentages given in Table 2.
[c]ND, Not determined.

APX-II has high percentage of Ala, Gly, Ser, and Thr. When the mature polypeptide was used for comparison, the overall amino acid composition was in fairly good agreement with that for APX-II (Table 7), but very different to that published for APX-I (Leathers, T. D., "Amino acid composition and partial sequence of xylanase from Aureobasidium," Biotechnol. Lett. (1988) 10:775–780), which after careful consideration of the data appears to be erroneous. We suggest that APX-I and APX-II are encoded by xynA. This is based on their almost identical N-terminal amino acid sequences, immunological and regulatory relatedness, and the presence of a single copy of the gene and the transcript (see below). The purified APX-I and APX-II differ in mass. Posttranslational modifications such as glycosylation, proteolysis, or both could contribute to this phenomenon. The sequence, Asn-X-Ser/Thr, required for N-linked glycosylation was not found in this polypeptide (Orlean, P. et al., "Analysis of glycoproteins from *Saccharomyces cerevisiae*," Methods Enzymol. (1991) 194:682–696). Therefore, it is suggested that the APX-II may be more glycosylated by O-linked oligosaccharides than APX-I. The xylanases consisted of high percentages of Ser (11.6%) and Thr (10.0%) residues. Thus, the extent of glycosylation of these residues may contribute to the differences in mass of APX-I and APX-II. More glycosylation was detected on APX-II than on APX-I using carbohydrate staining of protein bands on sodium dedocyl sulfate-polyacrylamide gel electrophoresis gels.

Homology of the sequence with other xylanases: The deduced amino acid sequence of xynA was used to search for the homologous sequences in the SWISS-PROT data base. This sequence had significant homology only with those of some xylanases. The alignments of these homologous sequences are given in Table 8. Table 8 shows alignments of homologous xylanase sequences to *A. pullulans* xynA sequence. Sequences listed include xylanases from *A. pullulans* in this study (XynA-Aurpu), *B. pumilus* (Xyna-Bapu), *R. flavefaciens* (Xyna-Rumfi), *S. lividans* B (Xynb-Strli) and C (Xync-Strli), *B. circulans* (Xyna-Baci), and *N. patriciarum* (Xyna-Neopa). Sequence identity was 45.6% for *Bacillus pumilus*, 33.8% for *Ruminococcus flaveficiens*, 41.4% and 38.7% for *Streptomyces lividans* B and C, 41.7% for *Bacillus circulans*, and 38.8% for *Neocallimastix patriciarum* xylanases (Gilbert, H. J. et al., "Homologous catalytic domains in a rumen fungal xylanase: evidence for gene duplication and prokaryotic origin," Mol. Microbiol. (1992) 6:2065–2072; Shareck, F. et al., "Sequences of three genes specifying xylanases in *Streptomyces lividans*," Gene (1991) 107:75–82). Certain regions shown in Table 8 including YGW at *A. pullulans* amino acid position 105–107, EYY at position 114–116, and TFKQYWSVRQ at position 165–174 (i.e. amino acids 131–140 of SEQ ID NO:16) were highly conserved among these enzymes. These residues should play critical roles in substrate binding and catalysis. X-ray crystallographic and site directed-mutagenesis studies suggested that Glu-121 and Glu-209 in a *B. pumilus* xylanase are essential for its active site, whereas Asp-48 was not as critical (Ko, E. P. et al. (1992), "Site-directed mutagenesis at aspartate and glutamate residues of xylanase from *Bacillus pumilus*," Biochem. J. 288:117–121). The sequence alignment (Table 8) strongly supported this statement since Glu-114 and Glu-208 in *A. pullulans* XYNA were conserved in all xylanases, whereas Gly-48 of *A. pullulans* xynA amino acid sequence was in the position of Asp-48 of *B. pumilus* xylanase. *A. pullulans* xynA was not significantly homologous to the cellobiohydrolase of *Cellulomonas fimi* and the xylanase Z of *Clostridium thermocellum*, which were the two representative enzymes to be classified as family F for β-glycanases using hydrophobic cluster analysis (HCA) (Henrissat, B. et al., "Cellulase families revealed by hydrophobic cluster analysis," Gene (1989) 81:83–95). In contrast, *A. pullulans* xynA deduced amino acid sequence was significantly homologous to Xln B and C of *S. lividans*, and Xln B of *R. flaveficiens*, which were recently classified as family G of β-glycanases (Gilkes, N. R. et al., "Domains in microbial β-1,4-glycanase: Sequence conservation, function, and enzyme families," Microbiol. Rev. (1991) 55:303–315). Thus, *A. pullulans* xynA may be grouped into this family.

Table 8

```
Xyna_Aurpu    1  MKFFAITLLFLVLGLYLAPIAEEAEAAEAPMLIEHECPGCINYVQNYYGN.L           SEQ ID:16
Xyna_Bacpu    1  MNLRKLRLLFVMCIGLWLLPTAVPAHARTHTNNEMGNHSGYDYLLWKDY.G           SEQ ID:17
Xyna_Rumfl    1  MKLSKIKKVLSGTVSALMLASAAPVVESAADQETRGNVGGYDYEMWNQN.G           SEQ ID:18
Xynb_Strli    1  ............VAHR..SPLMLPGTAFADHVTTNQEGTNNGYYSFWTDS.Q         SEQ ID:19
Xync_Strli    1  RGELEGAELALADASELLSALMPGTAFSATASANSTD.DGMYSFWTDG.G           SEQ ID:20
Xyna_Bacci    1  ...KNFLVGLSALMSISLFSATASANSTD......LWQNWTDG.G                SEQ ID:21
Xyna_Neopa    1  NPAPHETEMVPSSAGESTANGKKFTVGNGQNDHKGVNDGFSYEIWLDNTG           SEQ ID:22

Xyna_Aurpu   51  G.QFTYNENAGTYSMYMNNGVN.GEFVCGFGWSTGAAR.........SITY
Xyna_Bacpu   51  NTSMTLNNG.GAFSAGWNNI..GNAFFRKGKKFDSURTHHQ.LGNISINY
Xyna_Rumfl   51  QGQAEMNPGAGSFTCSWSNI..ENFEARMGKNYDBQKKNYKAFGNIVFTY
Xynb_Strli   41  GTVSMNMGSGGQYSTSWRNT..GNFVAGKGWANGCR.RT........VQY
Xync_Strli   50  GSVSMTLNGGGSYSTGWTNC..GNFVAGKGWSTGD.GN.........VRY
Xyna_Bacci   37  GIVNAVNGSGNYSNWSNT....GNFVVGKGWHTGSPFRT........INY
Xyna_Neopa   52  GNGSMTLGSGATFKAEWNAAVNRGFARRGLDFGSQKKATD.YDYIGLDY Xyna_Aurpu   91  S.SNYQ....ASGGSYLEVYGWINS.....PQAEYYIVESYGSYNPCGAGQ
Xyna_Bacpu   97  NAS.EN....PSGNSYLCVYGWTQS.....PLAEYYIVDSWGHYRPT....
Xyna_Rumfl   99  DVE.YT....PRGNSYMCVYGWTRN.....PLMEYYIVEGWGDWRPPG...
Xynb_Strli   80  G.GSFN....PSGNAYLAYGWTSN.....PLVEYYIVDNWGSYRPT....
Xync_Strli   88  N.GYEN....PVGNGYGCTYGWTSN.....PLVEYYIVPNWGSYRPT....
Xyna_Bacci   77  NAGVWA....PNGNGYLTHYGWTRS.....PLIEYYMVDSWGAYRPT....
Xyna_Neopa  102  HATYKQTASASGNSRLCVYGWFQNRGLNGVPLVEYYIIEDWVDWP.....

Xyna_Aurpu  132  SGVTQLGGTVCSDGATYTMYTDTRTNQPSITGT.STFKQYWSVRQTKRTS.
Xyna_Bacpu  134  ..GAYKGSFYADGGTYDIYETTERVNQPSIIGI..ATFKQYWSVRQTKRTS.
Xyna_Rumfl  137  NDGEVKGTVSAHGNTYDIYRKTMRYNQPSFDGT..ATFPQYWSVRQTSGSANN
Xynb_Strli  117  ..GEYKGTVTSDGGTYDIYKTTRVNKPSWEGTR...TFDQYWSVRQSKR..T..
Xync_Strli  125  ..GTYKGTVSSDGGTYDIYQTRVNAPSWEGTK...TFQQYWSVRQSKV.TSG
Xyna_Bacci  115  ..GTYKGTVKSDGGTYDIYTTTRYNAPSIDGT...TFQQYWSVRQSKRPTGS
Xyna_Neopa  148  .DAQGKMVTIDGAQYKIFQMDHITG.PHINGSSETFKQYFSVRQQKRTS..

Xyna_Aurpu  180  ........GTVTTGNHFAYWAKYG..FGNSYNEQVMPVEAFSGTGSASVTVS*  SEQ ID:16
Xyna_Bacpu  180  ........GTVTVSAHFRKWESLGMPM.GKMYETAFTVEGYQSGGSANVMTN. SEQ ID:17
Xyna_Rumfl  187  QTNYMKGTHDVTKHFDAWSAAGLDMSGILYEVSNHEGYRSNGSANVKSV.    SEQ ID:18
Xynb_Strli  162  ........GGTHTGNHFDAWARAGMPLGNFSYYMFWATEGYQSGHSSHNVG.  SEQ ID:19
Xync_Strli  172  ........SGTHTGNHFDAWARAGMNMCQFRYYMLWATEGYQSGSSNIVS.   SEQ ID:20
Xyna_Bacci  164  ........NATHTFTNHVNAHKSHGMNLGSNWALQVWATEGYQSAGSSNVTVW. SEQ ID:21
Xyna_Neopa  194  ........GHITVSDHFKEMAKQGWGIGN.LYEVALNAEGWQSGVADVTLL.  SEQ ID:22
```

Characterization of genomic DNA: Genomic DNA was digested with various restriction enzymes and Southern blot analysis was performed using the biotinylated PCR fragments as hybridization probes. Only one band was obtained for EcoRI (8.5 kbp), HindIII (9.4 kbp), EcoRI/HindIII (6.8 kbp), HaeIII (0.5 kbp), HaeIII/EcoRI (0.5 kbp), HaeIII/HindIII (0.5 kbp), and XhoI 1.0 kbp). The minor bands from HaeIII/EcoRI (3.0 kbp) and HaeIII/HindIII (6.5 kbp) digestions might be caused by incomplete digestion. These data indicated that the *A. pullulans* genome only possesses a single copy of this gene. Two 19-base oligonucleotide primers (PFW and PRW, Table 4) corresponding to the 5' and 3' ends of xynA were synthesized. Using these primers with genomic DNA and cDNA as templates, both genomic DNA and cDNA gave a band of approximately 900 bp after amplification by PCR. It appeared that the band amplified from genomic DNA was slightly larger than the one from cDNA, indicating that genomic DNA in this region might possess short introns. Sequencing of this region after cloning into pCRII and comparing the sequences revealed that it indeed had an intron of 59 bp. This intron sequence started with GTA and ended with TAG, which matched the general consensus sequences for intron ends (Davis, M. A. and Hynes, M. J., "Regulatory circuits in Aspergillus nidulans." In: J. W. Bennett and L. L. Lasure (eds.) More gene manipulations in fungi. Academic Press (1991) pp. 151–189; Rawn, D. J., "RNA Processing," Biochemistry, pp 781–820, Neil Patterson publishers, Carolina Biological Supply Company, Burlington, N.C. (1989)).

Example 5

Regulation of gene expression of xynA in *A. pullulans* by growth substrates The regulation of xynA expression by growth substrates was investigated with Northern blot analysis using the biotinylated PCR fragments as hybridization probes. An RNA band of about 900 bases was detected in cells grown in medium containing 1% (w/v) D-xylose or OSX, but not in medium containing 1% (w/v) glucose, 1% (w/v) D-xylose plus 1% (w/v) glucose, or 1% (w/v) OSX plus 1% (w/v) glucose. The intensity of the RNA bands from the samples of different cultures detected with ethidium bromide staining was similar. Three times as much cross-hybridization was obtained from medium containing OSX than from that containing D-xylose. This correlated with the levels of xylanase activity in the supernatants of OSX and D-xylose grown cells. Only one transcript is synthesized from this gene under induction. These results confirmed our suggestion that the expression is controlled at the transcriptional level rather than at the translational or posttranslational levels. Glucose behaved as a repressor. Xylan and D-xylose, the end product of xylan degradation, both are able to induce transcription only when glucose is absent or reaches certain low levels in the culture. Thus, the regulation of xylanase gene expression in *A. pullulans* must not parallel the cellulase gene expression in cellulolytic fungi such as *Trichoderma reesei*, in which glucose, the end product of cellulose degradation, completely represses the transcription of cellulose genes (El-Gogary, S. et al., "Mechanism by which cellulose triggers cellobiohydrolase I gene expression in *Trichoderma reesei*," Proc. Natl. Acad. Sci. USA (1989) 86:6138–6441).

Example 6

Expression of *Aureobasidium pullulans* xynA

Strains, plasmids, and genes: *E. coli* TOP10 and *S. cerevisiae* INSC1 (MATα, his3⁻Δ1, leu2, trp1⁻289, and ura3⁻52), and plasmid pYES2 were purchased from Invitrogen Corp. (San Diego, Calif.). pYES2 possesses ampicillin and tetracycline resistance genes for selection in *E. coli*, a URA3 gene for high-copy number maintenance and selection in ura⁻ *S. cerevisiae*, and a gal1 promoter sequence. cDNA of xynA from *A. pullulans* cloned by cDNA library construction and screening as well as polymerase chain reaction (PCR) amplification as described herein and sequenced as to the full open reading frame (ORF) using automatic DNA sequencing procedures was used.

Construction of plasmid cassettes. The plasmid pYES2 was digested by HindIII and BamHI. Digested plasmid was dephosphorylated with calf intestinal alkaline phosphatase and purified using the GenecleanII kit (Bio101, Inc., La Jolla, Calif.). Based on the nucleotide sequence of xynA, forward (PF3 and PF4) and reverse (PR) PCR primers (Table 9) were synthesized and used to amplify various regions of xynA.

TABLE 9

| | Oligonucleotide primers used for the amplification of PCR products for xynA expression. | |
|---|---|---|
| Name | Sequence* | |
| PF3 | CACACAAGCTTATGGCCGGTCCCGGTGGCATCAA | SEQ ID:23 |
| PF4 | CACAGAAGCTTGATCACATCCATTCAAACAAT | SEQ ID:24 |
| PR | CCTTCGGATCCTAGCAAGGTGTCTGACATTTA | SEQ ID:25 |
| PIN | ACAGAAGCTTATATGATGCTTTTGCAAGCCTTCCTT TTCCTTTTGGCTGGTTTTGCAGCCAAAATATCTGCA GCCGGTCCCGGTGGCATCAACT | SEQ ID:26 |
| PAF | ACAGAAGCTTAAAGAATGAGATTTCCTTCAATTTTT ACTGCAGTTTTATTCGCATCCTCCGCATTAGCTGCC GGTCCCGGTGGCATCAACT | SEQ ID:27 |

*All primers are written from 5' to 3'. HindIII and BamHI sites are underlined and double-underlined, respectively.

PF3 corresponded to the first 6 amino acids of the mature xylanase whereas PF4 was 19 bp upstream of the start codon of xynA. In order to insert the xylanase gene into pYES2 multiple cutting sites, PF3 and PF4 had a HindIII site whereas PR had a BamHI site attached. Using genomic DNA isolated from *A. pullulans* and its cDNA library as templates, xynA regions were amplified by PCR for 25 cycles on a 480 Thermocycler (Perkin Elmer Co., Norwalk, Conn.). Pfu polymerase from Stratagene Cloning Systems, La Jolla, Calif. was used for the amplification. For fusing the nucleotide sequences encoding the signal peptides of invertase and α-factor of *S. cerevisiae* to the DNA region encoding the mature xylanase, two long oligonucleotides (PIN and PAF) were designed and synthesized (Table 9). Using these two oligonucleotides as forward and PR as reverse primers, and A. pullulans genomic DNA as template, these two yeast signal peptides were fused to XYNA mature enzyme during PCR amplification. Each cycle included 1 min at 54° C. for annealing, 1 min at 94° C. for denaturation, and 2 min at 72° C. for extension. PCR products were purified using the GenecleanII kit, and digested by HindIII and BamHI overnight. DNA fragments were purified and concentrated using the GenecleanII kit before they were ligated to the prepared pYES2 by T4 ligase.

Transformation of E. coli and propagation of plasmids: Ligation reactions were used directly for the transformation of E. coli strain TOP10 (Invitrogen Co.) as described by Sambrook et al., "Molecular Cloning. A Laboratory Manual," 2nd Ed. Cold Spring Harbor, New York: Cold Spring Harbor Laboratory Press (1989). Transformation was plated out on LB plates containing 100 µg.ml$^{-1}$ ampicillin. Colonies were picked and grown overnight in LB medium containing ampicillin. Plasmids were purified using the spin column kit from Qiagen (Chatsworth, Calif.). Restriction digestion and nucleotide sequencing were done to verify the presence, orientation and sequence of the inserts.

Transformation of S. cerevisiae: A single colony of yeast strain INVSc1 was grown to an absorbance reading at 600 nm ($A_{600}$) of 1.3 in YPD medium, pH 6.5, containing 2% (w/v) peptone-Y, 1% (w/v) yeast extract-Y, and 2% (w/v) dextrose. Cells were harvested by centrifugation (5000× g, 5 min) at 4° C., washed twice with sterile $H_2O$ and twice with 1M sterile sorbitol. Cells were re-suspended in 2 ml 1M sorbitol. Approximately 5 µg plasmids were used to transform 40 µl prepared yeast cells using an electroporator (Bio-Rad Laboratory, Hercules, Calif.). Transformants were sprouted on dextrose (2%, w/v) SD uracil$^-$ agar medium containing 1M sorbitol and incubated for 3 days at 30° C.

Induction of gene expression: 500 ml flasks containing Raffinose (4%, w/v) SD uracil$^-$ medium (200 ml) were inoculated with single colonies of different transformants and shaken (250 rmp) at 30° C. for about 48 hr. Growth of transformants were monitored by measuring $A_{600}$ periodically. When $A_{600}$ of the cultures reached 2, sterile galactose was added to the cultures to a concentration of 2.0% (w/v). Aliquots of 10 ml were collected before and four hours after the addition of galactose. Cells in collected samples were removed from supernatants by centrifugation (5000× g, 5 min) at 4° C. All samples were kept at −20° C. until analyzed.

Isolation of RNA from S. cerevisiae and Northern blot analysis: S. cerevisiae transformant cells after 4 hr of induction by galactose were harvested by centrifugation (5,000× g, 5 min) and washed with $H_2O$ at 4° C. Wet cells (1 g) were subjected to RNA isolation by using the Total RNA Isolation Kit (Promega Corp., Madison, Wis.). RNA samples (10 µg) were separated on a formaldehyde agarose (1.5%, w/v) gel as described by Sambrook et al "Molecular Cloning. A Laboratory Manual," 2nd ed. Cold Spring Harbor, New York: Cold Spring Harbor Laboratory Press (1989) and transferred to a nylon membrane by using the Turboblotter (Schleicher & Schuell, Inc., Keene, N.H.). The full length cDNA of A. pullulans xynA was labelled with digoxigenin by PCR in the same way as was done for amplifying the expression cassettes. Using this DNA sequence as a hybridization probe, xylanase-specific mRNA bands on the membrane were detected as described herein.

Enzyme and protein assays: Remazol brilliant blue R-D-xylan (RBB-xylan) (0.2%, w/v) in 50 mM sodium acetate buffer, pH 4.5, was used as a substrate for routine xylanase assay, modified from Biely et al., "Soluble chromatogenic substrates for the assay of endo-1,4-β-xylanases and endo-1,4-β-glucanases," Anal. Biochem. (1985) 144:142–146. Reactions were carried out at 30° C. for 15 min with enzyme activity adjusted to its linearity. No activity unit can be directly calculated from this procedure. Thus, xylanase assay using birch wood xylan as described herein as substrate was used to calibrate and convert the absorption readings into activity units. One unit of enzyme activity was defined as the amount of enzyme that released 1 µmol of xylose equivalent per min. Protein was measured by using the BSA reagent from Pierce (Rockford, Ill.).

SDS-PAGE and N-terminal amino acid sequencing: Extracellular xylanase producing clones were grown in raffinose medium to an $A_{600}$ of 2 and further grown for 6 hours after the addition of galactose. Cells were removed by centrifugation. Supernatants, which contained the secreted xylanase, were concentrated by using tangential-flow ultrafiltration (Amicom, Inc., Beverly, Mass.) against a membrane (YM3) having an apparent molecular weight cutoff of 3,000. Concentrated samples were subject to sodium dodecyl sulfate (SDS)-polyacrylamide (12%, w/v) gel electrophoresis (PAGE) as described (Laemmli, U. K., "Cleavage of structural proteins during the assembly of the head of bacteriophage T4," Nature (London) (1970) 227:680–685. After electrophoresis, proteins were transferred to DVPF membrane at 4° C. in 20 mM Tris/HCL, pH 8.3, 20% (v/v) methanol and 0.1% SDS using a Mini Trans-Blot cell (Bio-Rad Laboratory). Transfer was done for 1 hr under a constant voltage of 80. Protein bands on the membranes were stained with Coomassie brilliant blue (CBB) R-250 for 5 min, and destained twice in a solution containing 10% (v/v) acetic acid and 40% (v/v) methanol for 5 min each. The xylanase band was identified by comparing the protein patterns of samples prepared before galactose induction. The xylanase band was cut out and subjected to amino terminal amino acid sequencing on 477A gas-phase sequencer (Applied Biosystems Inc., Foster City, Calif.).

Regions of genomic and cDNA sequences of xynA from A. pullulans were amplified (Table 9 and FIG. 1). For the expression of the mature enzyme, a Met codon was added in PF3 as an initiation codon of translation. DNA fragments were separated on agarose gels, excised after visualization by ethidium bromide staining, and purified. These fragments were cloned into pYES2 after they were digested by HindIII and BamHI. Ten colonies were picked and plasmid DNA was purified after E. coli cells were grown overnight in LB medium. The presence of inserts with proper sizes was detected with restriction analysis. For each construct, at least two plasmids were sequenced to confirm the fidelity during PCR amplification.

Figure 2:
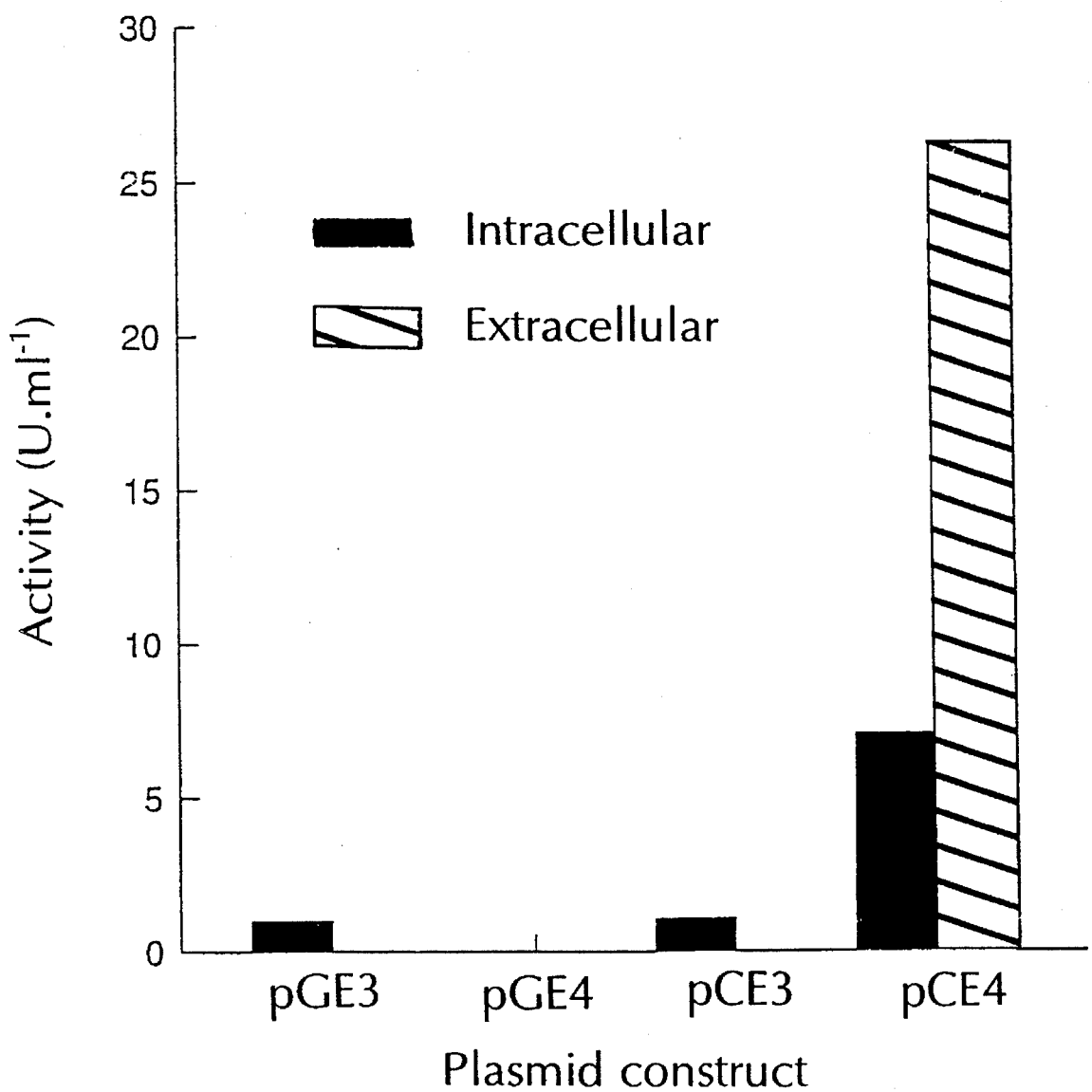
FIG. 2. Xylanase activity levels of *S. cerevisiae* INVSc1 transformed with various plasmid constructs. For each construct, one single colony was inoculated in 500 ml 4.0% (w/v) raffinose SD medium in a 1 liter flask. Flasks were shaken (225 rpm) at 30° C. to the cell density reaching an $A_{600}$ of 2. Sterile galactose was added to a concentration of 2.0% (w/v). Samples (10 ml) were withdrawn 4 hr after the addition of galactose.

Plasmids without mutation were used for the transformation of yeast cells. Four yeast clones containing PCR sequences amplified from genomic and cDNA samples were obtained and tested for xylanase production (FIG. 1, FIG. 2). Positive yeast colonies were grown in raffinose-SD medium to an $A_{600}$ of 2 and induced for the expression of xylanase gene by the addition of galactose. pGE3 and pCE3 contained DNA sequences amplified from genomic and cDNA templates, respectively, encoding the mature enzyme region. After four hours of galactose induction, similar levels (1.6 and 1.68 U.ml$^{-1}$) of xylanase activity were detected in cell associated preparations (FIG. 2). No activity was detected in the medium of these two cultures. No activity was detected in either cell associated or extracellular fractions of pGE4 containing DNA encoding the whole ORF. In contrast, high levels of xylanase activity were detected both in cell associated (6.7 U.ml$^{-1}$) and extracellular (26.2 U.ml$^{-1}$) fractions of pCE4.

The only difference between pGE4 and pCE4 was that pGE4 had the 59 bp long intron whereas pCE4 did not. Presumably, the intron sequence was not properly spliced in yeast cells during the expression of the xynA. Without splicing, the open reading frame of xynA could not read through during the translation. Therefore, no active enzyme could be synthesized. It has been noted that no internal recognition signal sequence in the xynA intron was found to match the ones commonly found in *S. cerevisiae* although 5' and 3' ends of the intron matched those of *S. cerevisiae* introns as described herein. Similarly, no proper splicing occurred when a *Cryptococcus albidus* xylanase (Moreau et al., "Secretion of a *Cryptococcus albidus* xylanase in *Saccharomyces cerevisiae*," Gene (1992) 116:109–113) and *Aspergillus awomori* glucoamylase (Innis et al., "Expression, glycosylation, and secretion of *Aspergillus glucoamylase* by *Saccharomyces cerevisiae*," Science (1985) 228:21–26) genomic DNA was cloned into *S. cerevisiae*. Nucleotide alterations of the internal recognition sequence of this intron by site direct mutagenesis should enable *S. cerevisiae* to splice the intron out.

It is interesting to note that activity levels between pCE3 and pCE4 were so different, especially between extracellular fractions (FIG. 2). Apparently, the difference was caused by the 34 amino acid signal peptide. It seems that the signal peptide not only led to the secretion of the enzyme but also increased the overall levels of the active enzyme synthesis. One explanation for these results is that the signal peptide was needed for high levels of secreted enzyme synthesis. Another explanation is that the newly synthesized enzyme was rapidly degraded in the absence of attachment to a signal peptide.

Figure 3:
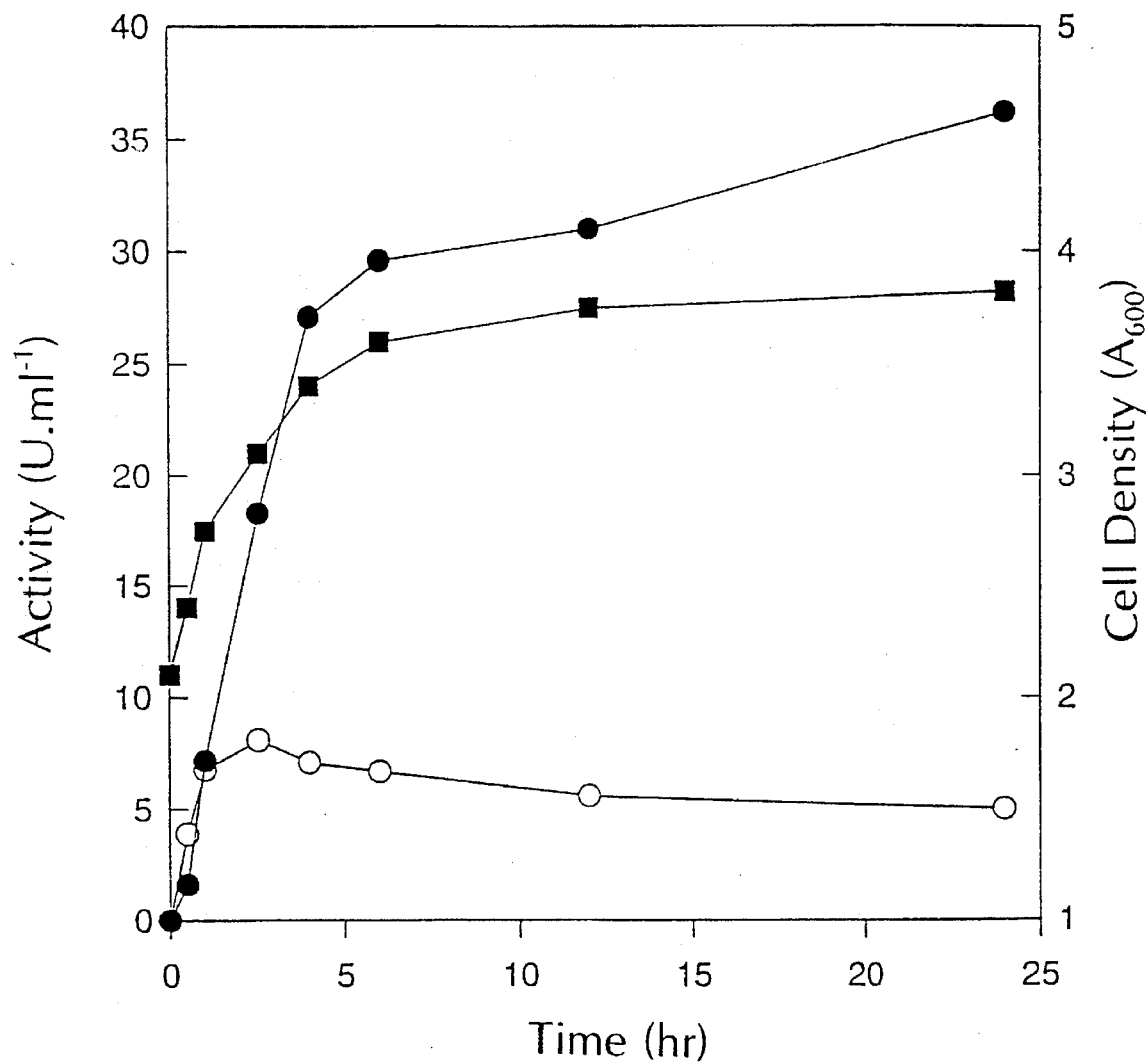
FIG. 3. Time course of xylanase induction of pCE4. One colony was inoculated to raffinose-SD medium and grown to an $A_{600}$ of 2. Sterile galactose was added and samples were withdrawn before and after the addition of galactose at time points shown above in the figure. Cell density (filled squares) was measured by reading the absorption value at 600 nm. Culture conditions, preparation of samples and enzyme assay were the same as for FIG. 2. Open circles represent cell-associated xylanase activity, and filled circles represent extracellular xylanase activity.

The study on pCE4 was carried on further. Cell associated and extracellular activity levels and cell density were measured after the addition of galactose (FIG. 3). The culture had a cell density of 2.0 at 600 nm after galactose was added. This value increased up to 3.78 after 24 hr with a sharp increase during the first 5 hr of induction. Cell-associated xylanase levels increased to their highest level (8.1 U.ml$^{-1}$) after 2.5 hr of induction, then slowly declined to about 6 U.ml$^{-1}$, and stayed low for the rest of the induction. In contrast, extracellular xylanase levels continually increased during the induction period (24 hr) although the fast increase was obtained during the first 4 hr. After 24 hr of induction, the extracellular xylanase level was 36 U.ml$^{-1}$, consisting of more than 85% of the total xylanase from both culture medium and cell-associated fraction. This secretion rate is extraordinary, considering that most proteins mediated by other signal peptides are confined in the cell wall or periplasmic space with only small percentages secreted (Emr et al., "An MFα 1-SUC2 (α-factor-invertase) gene fusion for study of protein localization and gene expression in yeast," Proc. Natl. Acad. Sci. USA (1983) 80:7080–7084; Das, R. C. and Shultz, J. L., "Secretion of heterologous proteins from *Saccharomyces cerevisiae*," Biotechnol. Progress (1987) 3:43–48; Moreau et al., "Secretion of a *Cryptococcus albidus* xylanase in *Saccharomyces cerevisiae*," Gene (1992) 116:109–113). Assuming that the recombinant xylanase has similar specific activity (2,000 U.ml$^{-1}$) as APX-I and APX-II do (Leathers, T. D., "Purification and properties of xylanase from Aureobasidium," J. Industr. Microbiol. (1989) 4341–348) the estimated xylanase concentration could be around 20 μg.ml$^{-1}$. This yield may be greatly improved by replacing gal1 promoter with constitutive promoters, integrating the expression cassette into chromosomal loci, and deleting the 3' untranslated sequence of xynA (Demolder et al., "Efficient synthesis of secreted murine interleukin-2 by *Saccharomyces cerevisiae*-influence of 3'-untranslated regions and codon usage," Gene (1992) 111:207–213).

Several types of yeasts are capable of fermenting xylose, the main component in hemicellulose, to ethanol and other chemicals (Mohanydas et al., "Development of xylose-fermenting yeasts for ethanol production at high acetic acid concentrations," Paper 16 In: Sixteenth Symp. on Biotech. for Fuels and Chemicals, (1994) Gatlinburg, Tenn.; Lu, Z. and Tsao, G. T., "Fermentation of xylose to glycerol by fungi," Poster 35 In: Sixteenth Symp. on Biotech. for Fuels and Chemicals, (1994) Gatlinburg, Tenn.). *S. cerevisiae* with a xylose isomerase gene expressed can ferment xylose to ethanol. Unlike enzymatic conversion of crystalline cellulose in plant cell wall to glucose, the conversion of xylan to xylose requires fewer enzymes and seems more efficient. In fact, a high percentage of the end-products of xylan hydrolysis by *A. pullulans* APX-II was xylose. In order to utilize xylan, a xylanase gene has to be expressed in these xylose-fermenting organisms with the active xylanase secreted into culture medium. *A. pullulans* xynA gene and its expression and secretion system in *S. cerevisiae* is perfect to incorporate into the above fermentation systems since this enzyme is so active on xylan and readily secreted from yeast.

Extracellular media of pCE4 culture before and after galactose induction were concentrated and subjected to SDS-PAGE analysis. Comparing the protein banding patterns of lanes loaded with these two samples, a protein band with a molecular mass of 27 kDa was identified as the band for the recombinant xylanase. The size of this xylanase was slightly larger than that (20 and 25 kDa) for APX-I and APX-II isolated from *A. pullulans*. To find out whether the retention of signal peptide or excessive glycosylation of the secreted enzyme causes the small mobility shift from APX-II, we determined the N-terminal amino acid sequence of this heterologously produced extracellular xylanase after it was separated on SDS-PAGE and transferred to a PVDF membrane. N-terminal amino acid sequence, AGPG-GINYVQNYNGNLG, of this heterologous xylanase was identical to that of mature xynA isolated from *A. pullulans* corresponding to amino acid 1–17 of SEQ ID NO:1). This result demonstrated that yeast cell secretion system recognized this signal peptide and efficiently translocated the synthesized protein. It is likely that this recombinant xylanase was slightly more glycosylated than APX-II from *A. pullulans*. Excessive glycosylation has been reported for a number of secreted recombinant proteins from yeast (Innis et al., "Expression, glycosylation, and secretion of *Aspergillus glucoamylase* by *Saccharomyces cerevisiae*," Science (1985) 228:21–26; Penttila et al., "Expression of two *Trichoderma reesei* endoglucanases in the yeast *Saccharomyces cerevisiae*," Yeast (1987) 3:175–185; Vainio, A. E. I. et al., "Cloning and Expression of *Hormoconis resinae* glucoamylase P cDNA in *Saccharomyces cerevisiae*," Curr. Genet. (1993) 24:38–44). A 24-amino-acid *Aspergillus awamori* glucoamylase signal peptide with an Arg-24 was recognized and removed when the gene was expressed in and its product was secreted from *S. cerevisiae* (Innis et al, "Expression, glycosylation, and secretion of Aspergillus glucoamylase by *Saccharomyces cerevisiae*," Science (1985) 228:21–26). Based on mutation studies, they demonstrated that the trypsin-like endopeptidase encoded by the yeast KEX2 gene, responsible for the maturation of α-factor in yeast, cleaved the peptide bond after Arg-24. Basic dipeptides Lys-Arg in yeast α factor (Achstetter, T. and Wolf, D. H. (1985), "Hormone processing and membrane-bound proteinases in yeast," Embo. J. 4:173–177) and *A. awamori* glucoamylase (Innis et al., (1985), "Expression, glycosylation, and secretion of an Aspergillus glucoamylase by *Saccharomyces cerevisiae*," Science 228:21–26) and Arg-Arg in human albumin (Collins, S. H., "Production of secreted proteins in yeast," pp. 61–77 In: T. J. R. Harris (ed.), Protein production by Biotechnology, Elsevier Applied Science, New York (1990)) are the signal motifs of this endopeptidase cleavage. It is not certain that KEX2 endopeptidase is also responsible for the processing of *A. pullulans* xynA from yeast since the dipeptide Glu-Arg at the C-terminus of XYNA signal peptide only have one basic residue. It should be pointed out that another cleavage by signal peptidase is necessary during the secretion process in yeast (Innis et al., "Expression, glycosylation, and secretion of Aspergillus glucoamylase by *Saccharomyces cerevisiae*," Science (1985) 228:21–26). Unlike endopeptidase, this peptidase requires an Ala residue at the amino side of the cleavage, as found for yeast invertase and α factor and *A. awamori* signal peptides. This cleavage might have occurred during XYNA secretion mediated by its own signal peptide from yeast since there are several Ala residues on the carboxyl side after the hydrophobic core of the signal peptide.

To compare the efficiency of xylanase secretion directed by XYNA signal peptide with that of invertase and α-factor, the two most commonly used signal peptides for heterologous protein secretion from *S. cerevisiae*, we synthesized the oligonucleotides (pIN and PAF) encoding the two signal peptides and the first 7 amino acids of the mature XYNA (Tables 9 and 10). Using PIN, PAF, and PR as primers and *A. pullulans* genomic DNA as template, signal peptides for the invertase and α-factor genes were fused in frame to the mature xylanase region of xynA by PCR amplification. After PCR products were digested with HindIII and BamHI, and inserted to pre-digested pYES2, and sequenced for confirming the lack of mutation during the PCR amplification, INVSc1 was transformed with these constructs (pIN1 and pAF1), together with pCE4 and pCE3. Single colonies of these transformants were tested for the extracellular xylanase production.

Figure 4:
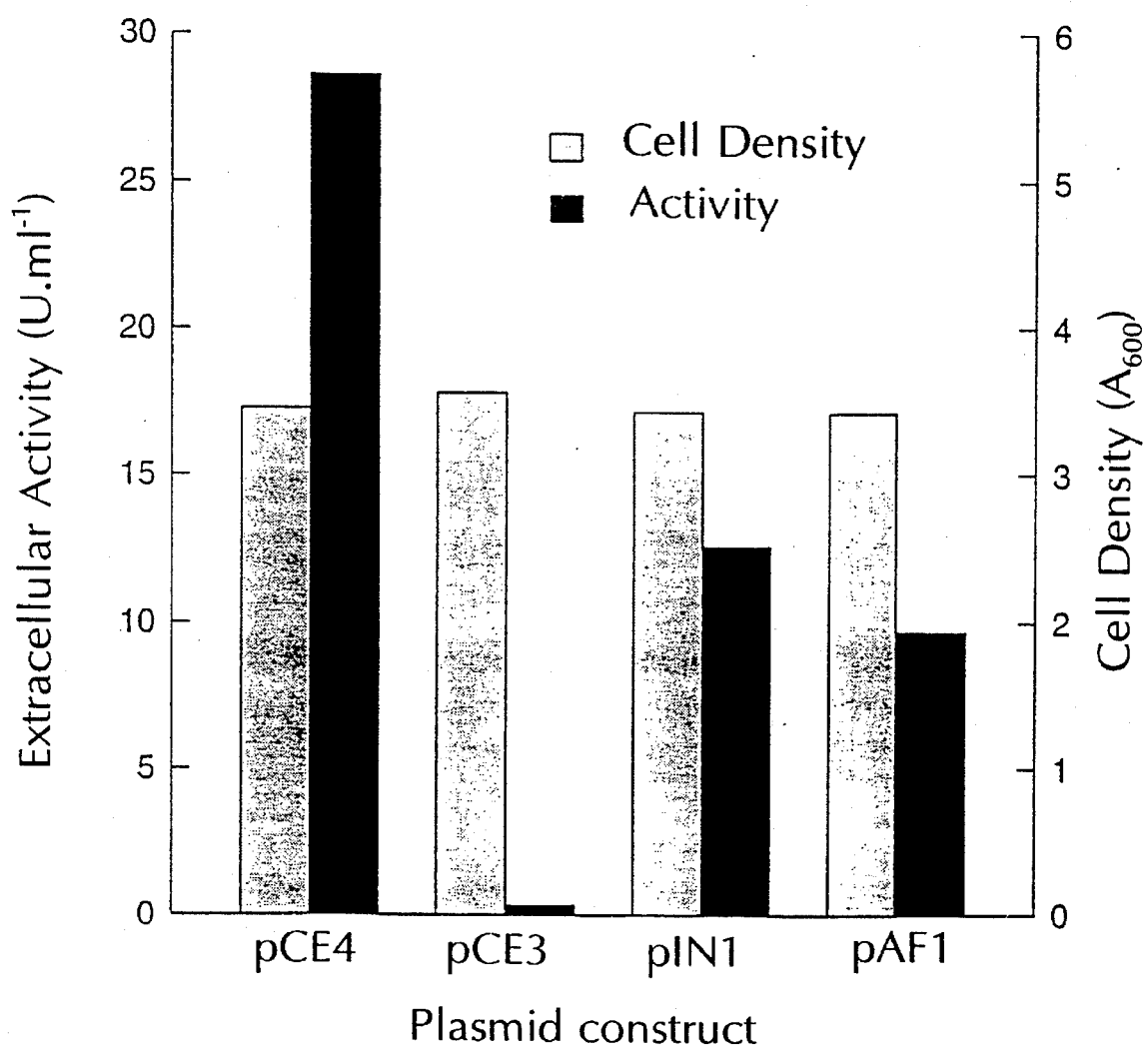
FIG. 4. Comparison of different signal peptides for the secretion of *A. pullulans* xylanase from *S. cerevisiae*. Single colonies of different yeast transformants were grown in 500 ml raffinose-SD medium in 1 liter flasks to an $A_{600}$ of 2.0. After 6 hr of induction by galactose, cell density and xylanase activity were determined. Culture and induction conditions and assays for cell density and xylanase were done as described for FIG. 2. pCE4, pIN1, and pAF1 represent pYES2 plasmids containing the DNA regions of mature *A. pullulans* xynA fused in frame to signal peptides of xynA, invertase, and α factor, respectively.

The four cultures after 6 hours of galactose induction had similar cell density (FIG. 4). Xylanase activity levels in the culture media, however, were different, with 28.6, 0.34, 12.6, and 9.7 $U.ml^{-1}$ for pCE4, pCE3, pIN1, and pAF1, respectively. Total RNA Samples were prepared from these four different clones after 6 hr of galactose induction. Northern blot analysis revealed that the xylanase specific mRNA levels between them were similar although the sizes of the mRNA bands between these clones was slightly different, due to the variation in their signal peptide regions (Table 10). It was also noticed that this heterologous mRNA was not stable in *S. cerevisiae* since a high percentage of incomplete mRNA was observed.

The low level of xylanase activity in the culture medium of pCE3 could be caused by leakage of intracellular xylanase out of dead cells. These results indicate that the XYNA signal peptide is more capable than the two yeast signal peptides for translocating the heterologous protein out of the yeast cells. The difference in the supernatant xylanase levels between these clones was related to the efficiency of secretion rather than transcription or translation. A longer hydrophobic region was found in the *A. pullulans* XYNA signal peptide than in the signal peptides of yeast invertase and α-factor and *A. awamori* glucoamylase (Table 10). The difference in length may be related to secretion efficiency, as is being demonstrated for prokaryotic signal peptides for secreting proteins out of *Bacillus subtilis*.

Further modifications of the invention herein disclosed will occur to persons skilled in the art who have the benefit of this disclosure, and all such modifications are deemed to be within the spirit and scope of the invention as defined by the appended claims.

We claim:

1. An isolated recombinant DNA molecule encoding a xylanase APX-II mature protein having the amino acid sequence set forth in SEQ ID NO:16 from amino acid 1 to 187.

2. The isolated recombinant DNA molecule of claim 1 additionally comprising the sequence ATG immediately 5' to the sequence encoding amino acid 1.

3. The recombinant DNA molecule of claim 1 having the nucleotide sequence as set forth in SEQ ID NO:15 from nucleotide 220 to 780.

4. The isolated recombinant DNA molecule of claim 3 additionally comprising the sequence ATG immediately 5' to nucleotide 221.

5. The recombinant DNA molecule of claim 1 encoding a xylanase APX-II mature protein and signal sequence having the amino acid sequence as set forth in SEQ ID NO:16 from amino acid −34 to 187.

6. The recombinant DNA molecule of claim 5 encoding a xylanase APX-II mature protein and signal sequence, said DNA molecule having a nucleotide sequence as set forth in SEQ ID NO:15 from nucleotide 59 to 780.

7. The recombinant DNA molecule of claim 5 encoding a xylanase APX-II mature protein and signal sequence, said DNA molecule having a nucleotide sequence as set forth in SEQ ID NO:15 from nucleotide 59 to 151 immediately 5' to the nucleotide sequence as set forth in SEQ ID NO:15 from nucleotide 211–219.

8. A *Saccharomyces cerevisiae* cell comprising the recombinant DNA molecule of claim 1.

9. A *Saccharomyces cerevisiae* cell comprising the recombinant DNA molecule of claim 5.

10. A method for producing xylanase APX-II in a host cell other than *Aureobasidium pullulans*, said method comprising the steps of:

(a) infecting or transforming a host cell capable of expressing xylanase coding regions with a vector comprising a promoter active in said host cell operably linked to the coding region for said xylanase APX-II, having an amino acid sequence as set forth in SEO ID NO:16 from amino acid 1 to 187.

11. An isolated recombinant DNA molecule comprising a nucleotide sequence encoding a signal peptide having an amino acid sequence as set forth in SEQ ID NO:16 from amino acid −34 to −1.

12. The recombinant DNA molecule of claim 11 having the nucleotide sequence as set forth in SEQ ID NO:15 from nucleotide 59 to 219.

13. The recombinant DNA molecule of claim 12 having the nucleotide sequence as set forth in SEQ ID NO:15 from nucleotide 59 to 151 immediately 5' to the nucleotide sequence as set forth in SEQ ID NO:15 from nucleotide 211–219.

14. An isolated recombinant DNA molecule wherein a nucleotide sequence encoding a signal peptide having the amino acid sequence as set forth in SEQ ID NO:16 from −34 to −1 is 5' to a heterologous coding sequence.

15. A *Saccharomyces cerevisiae* cell comprising the recombinant DNA molecule of claim 11.

16. A method for producing a heterologous protein in a host cell, said method comprising the steps of:

(a) infecting or transforming said host cell with a vector comprising a promoter active in said host cell operable linked to a signal sequence having an amino acid sequence as set forth in SEQ ID NO:16 from −34 to −1 and a coding sequence which does not encode an amino acid sequence as set forth in SEQ ID NO:16 from amino acid 1 to 187;

(b) culturing the infected or transformed cell under conditions suitable for gene expression.

* * * * *

UNITED STATES PATENT AND TRADEMARK OFFICE
CERTIFICATE OF CORRECTION

PATENT NO. : 5,591,619　　　　　　　　　　　Page 1 of 2

DATED : January 7, 1997

INVENTOR(S) : Xin-Liang et al.

It is certified that error appears in the above-identified patent and that said Letters Patent is hereby corrected as shown below:

On the cover page, Castanares reference, second line "coumaroy lesterase" should read --coumaroyl esterase--.

On the cover page, Collins reference, "(Harris, T.J. F. ed)," should read --(Harris, T.J.R., ed),--.

At page 2, first column, in the second Li reference, "Eviron." should read --Environ.--.

At page 2, second column, in the Sreekrishna reference, "Microbilogy," should read --Microbiology,--.

At page 2, second column, last reference, "Ci et al.," should read --Li et al.,--.

At column 4, line 19, "disulfate" should read --disulfide--.

At column 8, line 42, "AMS" should read --ASM--.

At column 18, line 7, "inetic" should read --kinetic--.

At column 31, line 40, "(250 rmp)" should read --(250 rpm)--.

At column 33, line 23, "direct" should read --directed--.

At column 33, line 46, "fast" should read --fastest--.

At column 34, line 27, "culture" should read --cultures--.

At column 34, line 43, "corresponding" should read --(corresponding--.

At column 35, line 13, "have" should read --has--.

At column 62, line 38, "operable" should read --operably--.

UNITED STATES PATENT AND TRADEMARK OFFICE
CERTIFICATE OF CORRECTION

PATENT NO. : 5,591,619

DATED : January 7, 1997

INVENTOR(S) : Li et al

It is certified that error appears in the above-identified patent and that said Letters Patent is hereby corrected as shown below:

On the cover page, Item [75], "Li Xin-Liang" should read --Xin-Liang Li--.

Signed and Sealed this

Twenty-first Day of April, 1998

Attest:

BRUCE LEHMAN

*Attesting Officer*   *Commissioner of Patents and Trademarks*